(12) United States Patent
Fields et al.

(10) Patent No.: US 11,717,521 B2
(45) Date of Patent: Aug. 8, 2023

(54) COMPOUNDS AND METHODS FOR TREATING OR PREVENTING ANTERIOR SEGMENT OCULAR DISORDERS AND/OR RETINAL DEGENERATIONS

(71) Applicant: YALE UNIVERSITY, New Haven, CT (US)

(72) Inventors: Mark Fields, New Haven, CT (US); Lucian Del Priore, Tarrytown, NY (US); Huey Cai, Montville, NJ (US); Denton Hoyer, West Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/923,492

(22) Filed: Jul. 8, 2020

(65) Prior Publication Data
US 2020/0338081 A1 Oct. 29, 2020

Related U.S. Application Data

(63) Continuation-in-part of application No. PCT/US2019/012749, filed on Jan. 8, 2019.

(60) Provisional application No. 62/614,757, filed on Jan. 8, 2018, provisional application No. 62/716,546, filed on Aug. 9, 2018.

(51) Int. Cl.
*A61K 47/40* (2006.01)
*A61K 9/00* (2006.01)
*A61K 31/519* (2006.01)
*A61K 9/19* (2006.01)

(52) U.S. Cl.
CPC ............ *A61K 31/519* (2013.01); *A61K 47/40* (2013.01); *A61K 9/0051* (2013.01); *A61K 9/19* (2013.01)

(58) Field of Classification Search
CPC ............ A61K 31/4412; A61K 31/4418; A61K 31/519; A61K 47/40; A61K 9/0048; A61K 9/0051; A61K 9/19; A61P 27/02
See application file for complete search history.

(56) References Cited

U.S. PATENT DOCUMENTS

| 7,666,880 | B2 | 2/2010 | Lee et al. | |
|---|---|---|---|---|
| 8,158,609 | B1 * | 4/2012 | Marsh | A61K 47/40 514/58 |
| 9,617,266 | B2 | 4/2017 | Hoelzemann et al. | |
| 2009/0124612 | A1 | 5/2009 | Albrecht et al. | |
| 2009/0226422 | A1 | 9/2009 | Chaudhary et al. | |

FOREIGN PATENT DOCUMENTS

| WO | 2006082588 A2 | 8/2006 |
|---|---|---|
| WO | 2009035534 A2 | 3/2009 |

OTHER PUBLICATIONS

International Search Report and Written Opinion, dated May 23, 2019, for International Patent Application No. PCT/US2019/012749.
PUBCHEM-CID: 16474885 Create Date: Jul. 30, 2007 (Jul. 30, 2007) pp. 1-6. p. 2, structure.
PUBCHEM-CID: 50258 Create Date: Aug. 8, 2005 (Aug. 8, 2005) pp. 1-15. p. 2, structure.
Bohn, et al. "Dermatopharmacology of ciclopirox nail lacquer topical solution 8% in the treatment of onychomycosis" Journal of the American Academy of Dermatology 43.4 (2000): S57-S69. Abstract.
Farinelli, et al. "Cell cycle blockers mimosine, ciclopirox, and deferoxamine prevent the death of PC12 cells and postmitotic sympathetic neurons after removal of trophic support." Journal of Neuroscience 16.3 (1996): 1150-1162.
Choi, et al. "Ciclopirox prevents peroxynitrite toxicity in astrocytes by maintaining their mitochondrial function: a novel mechanism for cytoprotection by ciclopirox." Neuropharmacology 43.3 (2002): 408-417. Abstract.
Heffelfinger, et al. "SK HEP-1: a human cell line of endothelial origin." In Vitro Cellular & Developmental Biology-Animal 28.2 (1992): 136-142. Abstract.
Kupperman, Allan , et al., "Anti-inflammatory effectiveness of topically administered corticosteroids in the cornea without epithelium", Investigative Opthalmology, vol. 14, No. 3: 252-255. 1975.
McGhee, C.N.J. , et al., "Penetration of Synthetic Corticosteroids into Human Aqueous Humour" Eye. 1990. 4: 526-530.
Musson, D.G. , "An In Vitro Comparison of the Permeability of Prednisolone, Prednisolone Sodium Phosphate, and Prednisolone Acetate Across the NZW Rabbit Cornea", Journal of Ocular Pharmacology. 1992. vol. 8, No. 2: 139-150.
Schoenwald, R.D. , et al., "Effect of Particle Size on Opthalmic Bioavailability of Dexamethasone Suspensions in Rabbits", Journal of Pharmaceutical Science, Apr. 1980. vol. 69, No. 4: 391-394.
Sieg, James W., et al., "Vehicle Effects on Ocular Drug Bioavailability I: Evaluation of Fluorometholone", Journal of Pharmaceutical Science, Jun. 1975. vol. 64 (6): 931-936.

* cited by examiner

Primary Examiner — Sarah Pihonak
(74) Attorney, Agent, or Firm — Saul Ewing LLP; Kathryn Doyle; Domingos J. Silva

(57) ABSTRACT

The invention provides a method of treating retinal degenerations, such as but not limited to anterior segment ocular disorders and/or age-related macular degeneration (AMD), in a subject, the method comprising administering to the subject a pharmaceutical composition comprising an effective amount of a compound of formula (1) or formula (2). In a further aspect, the invention provides compounds of formula (2). In certain embodiments, the compounds of the invention prevent or minimize cellular assault, such as oxidative stress-related cellular assault, and/or promote cell viability.

9 Claims, 19 Drawing Sheets

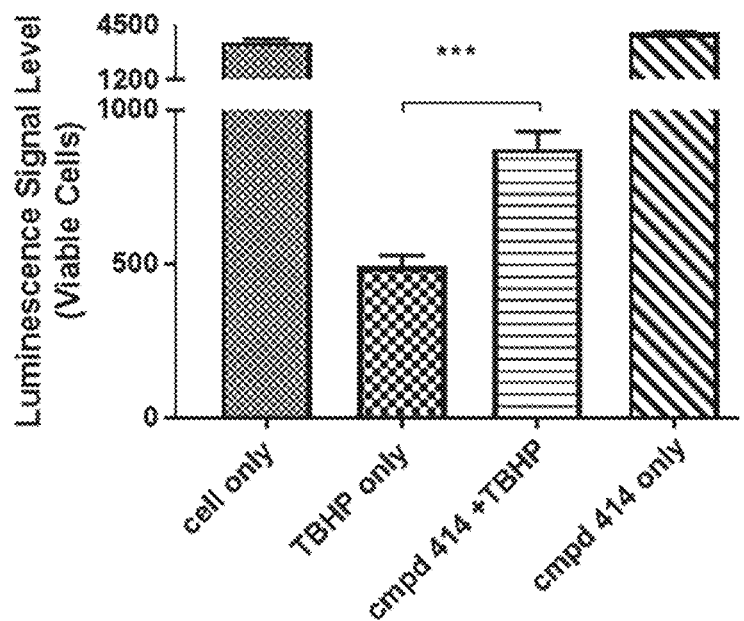
FIG. 8A
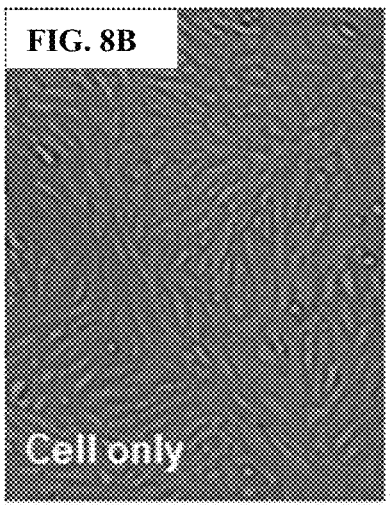
FIG. 8B — Cell only
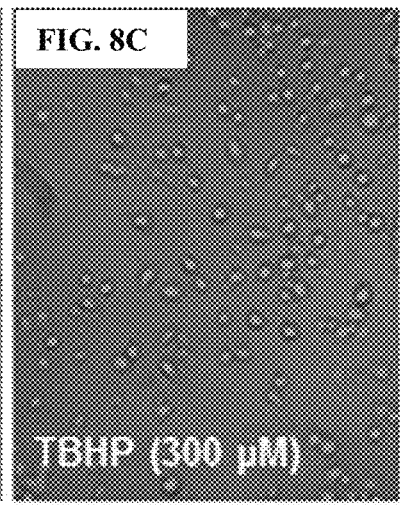
FIG. 8C — TBHP (300 μM)
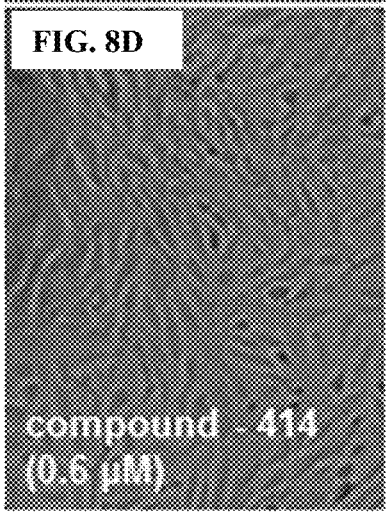
FIG. 8D — compound-414 (0.6 μM)
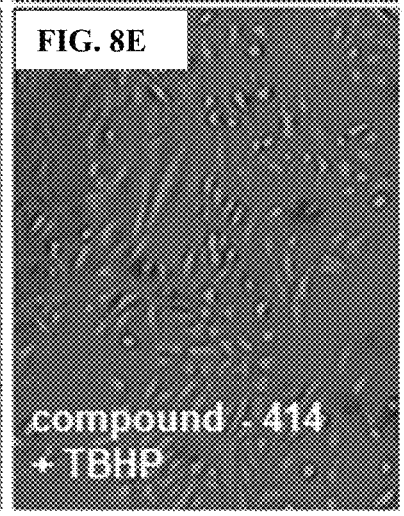
FIG. 8E — compound-414 +TBHP

*** P< 0.001 compound 414 compound 434

COMPOUNDS AND METHODS FOR TREATING OR PREVENTING ANTERIOR SEGMENT OCULAR DISORDERS AND/OR RETINAL DEGENERATIONS

CROSS-REFERENCE TO RELATED APPLICATIONS

The present application is a continuation-in-part, and claims priority to, PCT International Application No. PCT/US2019/012749, filed Jan. 8, 2019, and published under PCT Article 21(2) in English, which claims priority under 35 U.S.C. § 119(e) to U.S. Provisional Applications No. 62/716,546, filed Aug. 9, 2018, and No. 62/614,757, filed Jan. 8, 2018, all of which applications are incorporated herein by reference in their entireties.

BACKGROUND OF THE INVENTION

Retinal degenerations are a leading cause of untreatable blindness worldwide. There are many forms of this disease, including retinitis pigmentosa (RP), which is known to be caused by around 200 different gene defects; choroideremia; and age-related macular degeneration (AMD), which is the leading cause of blindness in elderly patients, affecting more than 8 million individuals in the US alone. Given the large number of patients with retinal degenerations, and the rapid increase in the aging population, the number of patients affected by these disorders is expected to increase in the future.

Aside from vitamins and antioxidants recommended by the Age-Related Eye Disease Study, there is no effective therapy for 90% of AMD patients with "dry" or atrophic AMD. Other retinal degenerations mentioned above have no known treatments. Therapies are needed to slow or retard the development and progression of retinal disorders. As a specific example, there is a need to develop effective strategies to limit the progression of geographic atrophy (GA) and to prevent progression from dry to wet AMD. The AMD treatment market alone in the U.S., UK, Germany, France, Spain, Italy, and Japan will double in value from $5.3 billion in 2015 to $10.1 billion in 2023

The retinal pigment epithelial (RPE) cells are vital for proper functioning neurosensory retina. The cells make up a portion of the RPE-Bruch's membrane-choroid complex and perform critical functions for maintaining vision, including phagocytosis of photoreceptor outer membranes, processing of retinoids, and polarized secretion of factors such as vascular endothelial growth factor (VEGF) and pigment epithelium-derived factor (PEDF).

Age-related changes in RPE cells are a hallmark of early AMD and contribute to pathology and visual morbidity associated with advanced AMD. Oxidative stress is a contributing factor to these changes and has been implicated in other diseases in which aging is a risk factor, including Alzheimer's disease and Parkinson's disease. In addition, Mendelian disorders, such as most forms of RP, can be accelerated by the presence of oxidative stress. In vitro and in vivo studies demonstrate that oxidative stress can accelerate cone photoreceptor death in animal models of RP.

Diseases of the anterior segment including the cornea, lens, and trabecular meshwork are leading causes of blindness worldwide. Oxidative stress and mitochondrial function has been implicated in these anterior segment diseases, including but not limited to such as Fuchs endothelial corneal dystrophy (FECD), cataracts, glaucoma, and keratoconus.

Age-related changes in cornea endothelial cells are a hallmark of FECD and contribute to pathology and visual morbidity. FECD is a progressive, bilateral disease characterized by a gradual loss of corneal endothelial cells (CECs; Elhalis, et al., 2010, Ocul. Surf 8:173-184). Loss of CECs impairs the ability of the cornea to maintain hydration, and results in a progressive decline in corneal transparency and hence a decline in vision. FECD is estimated to affect about 4% of the population, mostly in their forties and fifties. CECs are a highly metabolic cell type, exposure to sunlight and the lack of a significant capacity for natural regeneration of CECs make them susceptible to mitochondrial dysfunction and oxidative damage (Jurkunas, et al., 2010, Am. J. Pathol. 177:2278-2289). Increased oxidative stress in the FECD cornea contributes to endothelial oxidative DNA damage, morphological modification and CEC apoptosis.

Age-related cataracts are a leading cause of loss of vision among elderly individuals affecting approximately 46% of 180 million visually disabled people worldwide. Age-related changes in lens epithelial cells are a hallmark of cataract formation and contributes to pathology and visual morbidity. Increased oxidative stress is caused by factors such as ultraviolet light and hydrogen peroxide, and both are risk factors for cataract development. At present, the only effective treatment is extraction of cataractous lens followed by implantation of an artificial intraocular lens (IOL). However, this surgery carries some inherent risks of post-operative complications such as stimulation of chronic inflammation, cystoid macular edema, corneal edema, endophthalmitis, retinal detachment, vitreous hemorrhage and other disorders. Moreover, inadequate surgical facilities and the high cost of artificial IOLs can be major limitations to treatment in developing countries.

Keratoconus is leading cause of corneal transplantation in younger individuals, accounting for approximately 25% of all transplants. Chronic keratocyte apoptosis, particularly of the anterior stromal keratocytes, can lead to stromal thinning in keratoconus (Kim, et al., 1999, Invest. Ophthalmol. Vis. Sci. 40:35-42; Thalasselis, 2005, Ophthalmic Physiol. Opt. 25:7-12). Oxidative stress is one of the key factors that contributes to keratoconus pathogenesis (Kenney, et al., 2005, Invest. Ophthalmol. Vis. Sci. 46:823-832; Chwa, et al., 2008, Invest. Ophthalmol. Vis. Sci. 49:4361-4369).

Oxidative stress, including oxidative damage to trabecular meshwork cells, has been implicated in the pathogenesis of glaucoma (Izzotti, et al., 2006, Mutat. Res. 612:105-114). It has been demonstrated that there is a statistically significant correlation between oxidative DNA damage and daily mean, minimum, and maximum intraocular (IOP) values (Sacca, et al., 2005, Arch. Ophthalmol. 123:458-463).

Thus, there is a need for early interventions that protect or rescue RPE as such an intervention would be beneficial and prevent disease progression. Further, there is a need for compositions and methods for treating or preventing anterior segment disorders, such as but not limited to Fuchs endothelial corneal dystrophy (FECD), cataracts, glaucoma, and/or keratoconus. The present disclosure addresses this need.

BRIEF SUMMARY OF THE INVENTION

The present invention provides a method of treating or preventing retinal degeneration in a subject. The present invention further provides a method of treating or preventing an anterior segment ocular disorder. The present invention further provides a method of treating, ameliorating, or preventing cell death in a subject. The present invention further provides a method of promoting cell viability, in a subject. The present invention further provides certain compounds, or a salt, solvate, or prodrug thereof. The present invention further provides pharmaceutical compositions comprising certain compounds.

In certain embodiments, the method comprises administering to the subject a pharmaceutical composition comprising an effective amount of a compound of formula (1):

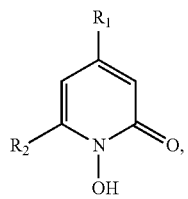
(1)

wherein $R_1$ is $C_1$-$C_3$ alkyl, $R_2$ is $C_1$-$C_{10}$ alkyl or $C_3$-$C_7$ cycloalkyl; or a salt, solvate, or prodrug thereof.

In certain embodiments, the method comprises administering to the subject a pharmaceutical composition comprising an effective amount of a compound of formula (1):

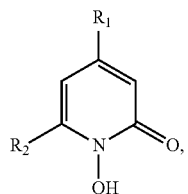
(1)

wherein $R_1$ is $C_1$-$C_3$ alkyl, $R_2$ is $C_1$-$C_{10}$ alkyl or $C_3$-$C_7$ cycloalkyl; and wherein the compound is not ciclopirox (6-cyclohexyl-1-hydroxy-4-methyl-2(1H)-pyridone); or a salt, solvate, or prodrug thereof.

In certain embodiments, the compound of formula (1) is not ciclopirox (6-cyclohexyl-1-hydroxy-4-methyl-2(1H)-pyridone), or a salt, solvate, or prodrug thereof.

In certain embodiments, the method comprises administering to the subject a pharmaceutical composition comprising an effective amount of a compound of formula (2):

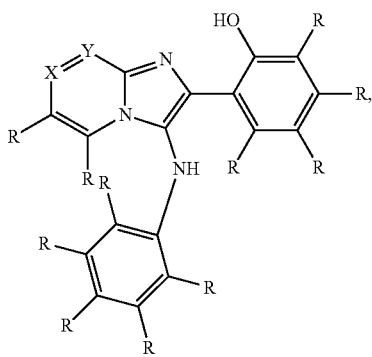
(2)

wherein one of X or Y is N and the other is CR; and wherein each instance of R is independently selected from the group consisting of H, $C_1$-$C_3$ alkyl, and halogen;

In certain embodiments, the retinal degeneration comprises age-related macular degeneration (AMD).

In certain embodiments, the disorder comprises at least one selected from the group consisting of Fuchs Endothelial Corneal Dystrophy, cataracts, glaucoma, and keratoconus.

In certain embodiments, in (1) $R_1$ is methyl.

In certain embodiments, in (1) $R_2$ is cyclohexyl. In certain embodiments, in (1) $R_2$ is 2,4,4-trimethyl-pent-1-yl.

In certain embodiments, the compound of formula (1) is piroctone (1-hydroxy-4-methyl-6-(2,4,4-trimethylpentyl)-2(1H)-pyridone). In certain embodiments, the compound of formula (1) is piroctone.

In certain embodiments, the compound of formula (2) is a compound of formula (3):

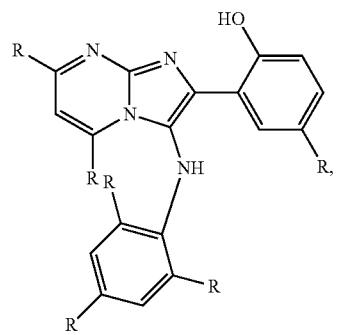
(3)

wherein each instance of R is independently selected from the group consisting of H, $C_1$-$C_3$ alkyl, and halogen.

In certain embodiments, the compound of formula (2) is a compound of formula (4):

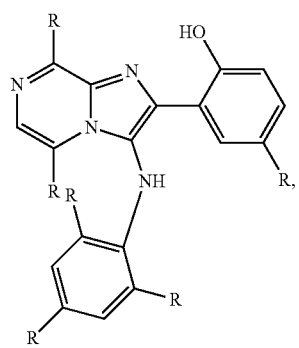
(4)

wherein each instance of R is independently selected from the group consisting of H, $C_1$-$C_3$ alkyl, and halogen. In certain embodiments, the compound of formula (2) is selected from the group consisting of:

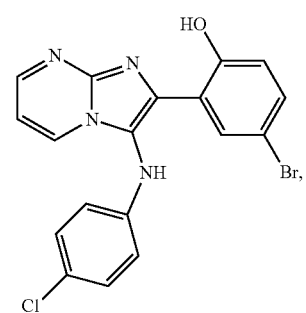

(5)

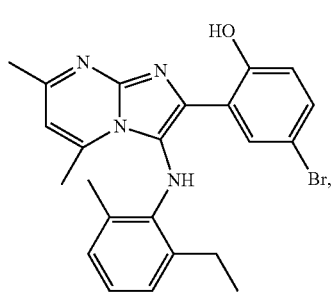

(6)

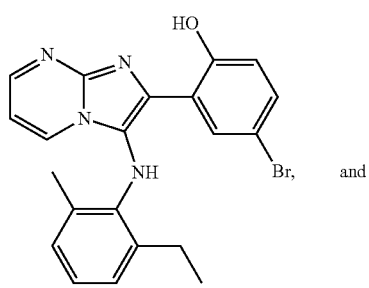

(7)

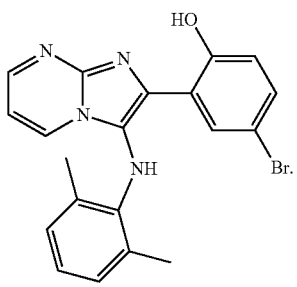

(8)

In certain embodiments, the pharmaceutical composition is formulated for ocular administration.

In certain embodiments, the cell death comprises oxidative stress-induced cell death.

In certain embodiments, the cell comprises a lens epithelial cell.

In certain embodiments, the cell death is associated with at least one disease selected from the group consisting of heart failure and other cardiovascular; pulmonary fibrosis; kidney disease; diabetic macular edema and retinopathies; neurodegeneration; mitochondrial myopathy; Barth's syndrome; and liver disease.

In certain embodiments, the compound is a compound of formula (2):

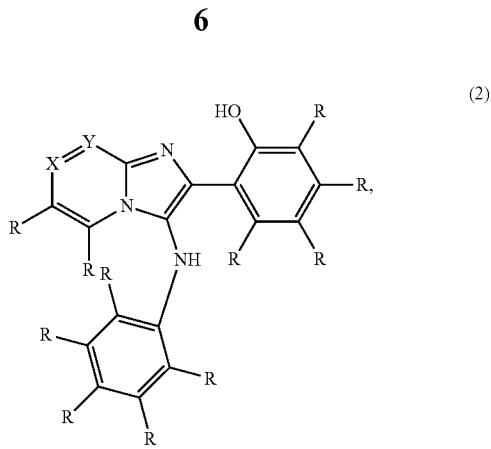

(2)

wherein one of X or Y is N and the other is CR, and wherein each instance of R is independently selected from the group consisting of H, $C_1$-$C_3$ alkyl, and halogen, or a salt, solvate, or prodrug thereof.

In certain embodiments, the compound is a compound of formula (3):

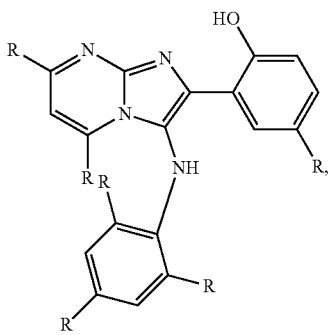

(3)

wherein each instance of R is independently selected from the group consisting of H, $C_1$-$C_3$ alkyl, and halogen.

In certain embodiments, the compound is a compound of formula (4):

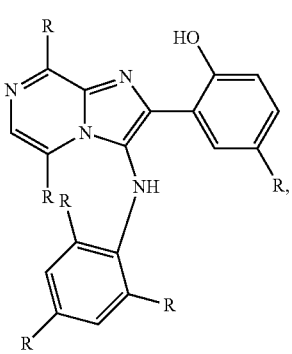

(4)

wherein each instance of R is independently selected from the group consisting of H, $C_1$-$C_3$ alkyl, and halogen. In certain embodiments, the compound is selected from the group consisting of:

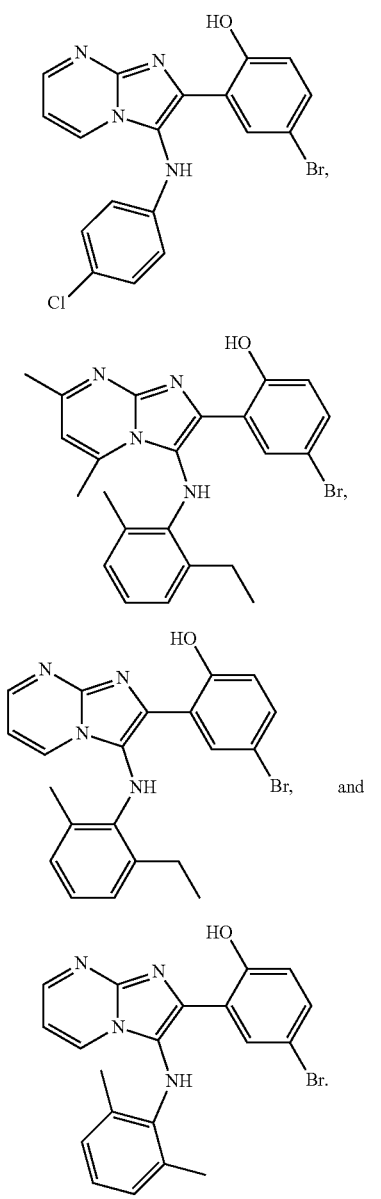

(5)
(6)
(7) and
(8)

In certain embodiments, the pharmaceutical composition comprises at least one compound of the invention. In certain embodiments, the pharmaceutical composition further comprises at least one pharmaceutically acceptable excipient. In certain embodiments, the pharmaceutical composition is formulated for ocular administration In certain embodiments, the pharmaceutical composition comprises a cyclodextrin, such as but not limited to gamma cyclodextrin (γ-cyclodextrin). In certain embodiments, the pharmaceutical composition comprises a cyclodextrin, such as but not limited to hydroxypropyl-beta-cyclodextrin (HPBCD). In certain embodiments, the pharmaceutical composition has pH of about 5-8. In certain embodiments, the pharmaceutical composition is a solution. In certain embodiments, the pharmaceutical composition is a suspension. In certain embodiments, the pharmaceutical composition is lyophilized. In certain embodiments, the pharmaceutical composition further comprises a thickening agent.

BRIEF DESCRIPTION OF THE DRAWINGS

The following detailed description of illustrative embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 1B depicts cells alone (control). FIG. 1C depicts cells treated with 300 µM TBHP. FIG. 1D depicts cells treated with 0.9 µM of ciclopirox olamine. FIG. 1E depicts cells treated with 0.9 µM of ciclopirox olamine and 300 µM TBHP, thus showing that ciclopirox olamine helps to preserve a normal morphology after challenge with TBHP.

FIG. 4A depicts basal respiration. FIG. 4B depicts maximal respiration. FIG. 4C depicts spare respiratory capacity. FIG. 4D depicts adenosine triphosphate (ATP) production. Each characteristic was significantly reduced in TBHP-treated cells compared to control, whereas ciclopirox olamine treatment increased all mitochondrial metabolic parameters studied when compared to TBHP-treated group. P<0.05, *P<0.001.

FIG. 7A depicts basal respiration. FIG. 7B depicts maximal oxygen consumption rate (OCR). FIG. 7C depicts spare respiratory capacity. FIG. 7D depicts ATP production. Each characteristic was significantly increased in ciclopirox olamine treated cells compared to TBHP-treated group. P<0.05, *P<0.001.

FIG. 8A shows that treatment with compound 414 significantly enhances cell viability after challenge with TBHP as measured by luminescence. p<0.05, *p<0.01. FIG. 8B depicts cells alone (control). FIG. 8C depicts cells treated with 300 μM TBHP. FIG. 8D depicts cells treated with 0.6 μM compound 414. FIG. 8E depicts cells treated with 0.6 μM compound 414 and 300 μM TBHP, thus showing that treatment with compound 414 helps to preserve a normal morphology after challenge with TBHP.

FIG. 9A depicts basal respiration. FIG. 9B depicts spare respiratory capacity. FIG. 9C depicts maximal respiration. FIG. 9D depicts ATP production. Each characteristic was significantly reduced in TBHP-treated cells compared to control, whereas treatment with compound 414 and 434 increased all mitochondrial metabolic parameters studied when compared to TBHP-treated group. P<0.05, *P<0.001.

FIG. 12A depicts basal respiration. FIG. 12B depicts maximal respiration. FIG. 12C depicts spare reserve capacity. FIG. 12D depicts ATP production. Each characteristic was significantly increased in compound 414 treated cells compared to TBHP-treated group. **P<0.05.

DETAILED DESCRIPTION

Definitions

Figure 1A:
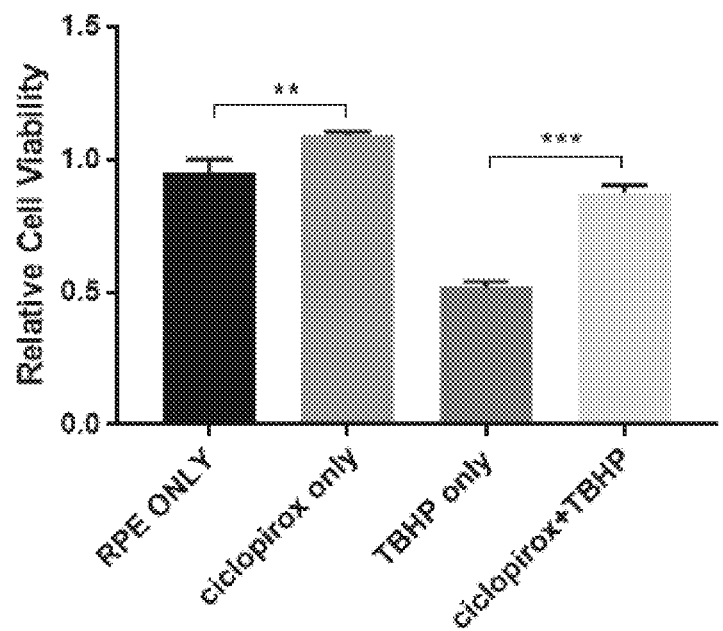
FIG. 1A is a graph that shows that treatment of retinal cells (in this case, retinal pigment epithelium, or RPE) with ciclopirox olamine (6-cyclohexyl-1-hydroxy-4-methyl-2 (1H)-pyridone, ethanolamine salt) significantly enhances cell viability after challenge with tert-butyl hydroperoxide (TBHP) as measured by luminescence. p<0.05, *p<0.01. Treatment with ciclopirox olamine alone also significantly enhances cell viability in human RPE cells compared to no treatment.
Figure 1A:
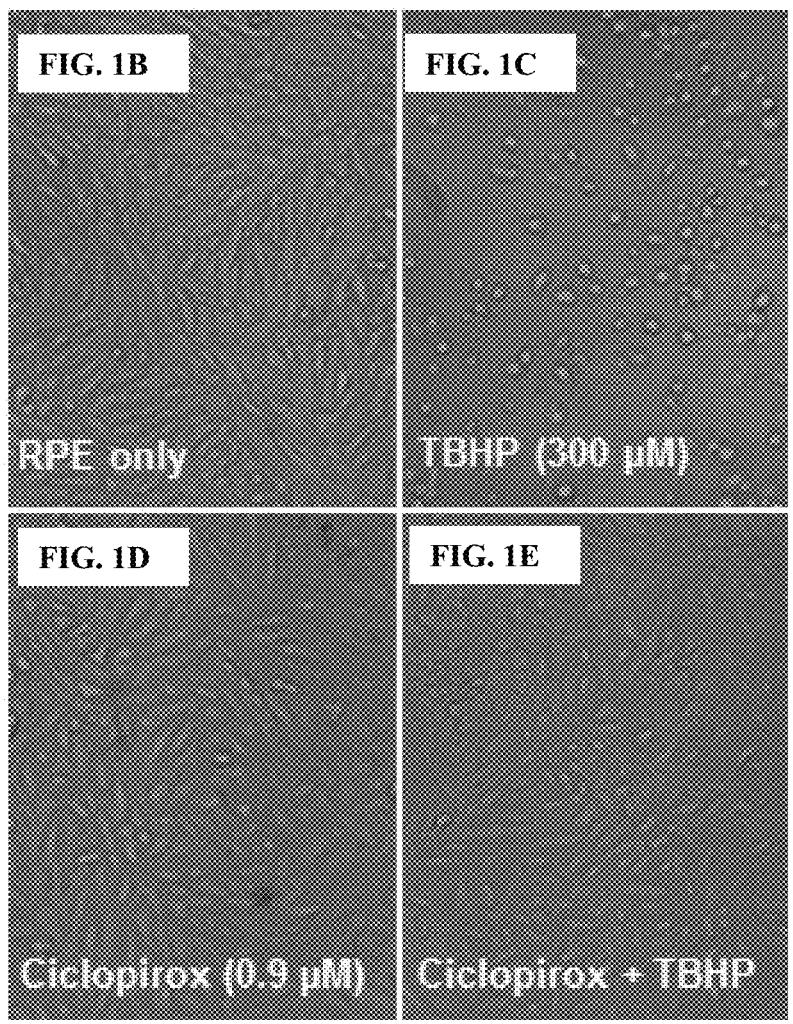

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, (including but not limited to topical, subconjunctival, subTenon's, suprachoroidal, intravitreal, or subretinal), pulmonary and topical administration.

As used herein, "compound 414" or "YU162779-01" refers to ChemDiv library compound number C325-0414, or a salt, solvate or hydrate thereof, having the formula:

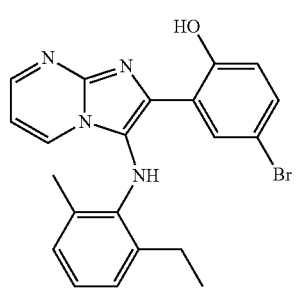

(7)

As used herein, "compound 434" or "YU162787-01" refers to ChemDiv library compound number C325-0434, or a salt, solvate or hydrate thereof, having the formula:

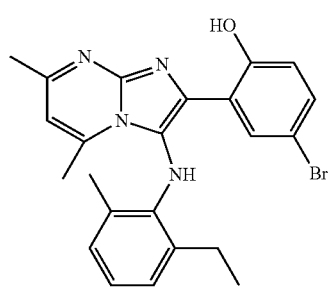

(6)

An "effective amount" or "therapeutically effective amount" of a compound is that amount of compound that is sufficient to provide a beneficial effect to the subject to which the compound is administered. An "effective amount" of a delivery vehicle is that amount sufficient to effectively bind or deliver a compound.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, substrate, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, "treating a disease or disorder" means reducing the frequency with which a symptom of the disease or disorder is experienced by a patient. Disease and disorder are used interchangeably herein.

As used herein, the term "treatment" or "treating" encompasses prophylaxis and/or therapy. Accordingly, the compositions and methods of the present invention are not limited to therapeutic applications and can be used in prophylactic ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In its various aspects and embodiments, the invention provides compounds and methods for the prevention and amelioration of retinal degenerations, including but not limited to AMD. In its various aspects and embodiments, the invention provides compounds and methods for the prevention and amelioration of anterior segment ocular disorders, such as but not limited to Fuchs endothelial corneal dystrophy (FECD), cataracts, glaucoma, and/or keratoconus. Without wishing to be limited by theory, in certain embodiments these compounds protect retinal cells, such as RPE cells, from cell death, in a non-limiting example oxidative stress-induced cell death. In other embodiments, these compounds protect retinal cells, such as RPE cells, from cell death on damaged extracellular matrix. In yet other embodiments, these compounds increase cell viability, wherein the cell is for example a lens epithelial cell. Administration of these compounds can induce expression of oxidative stress and anti-apoptotic related genes, thereby treating retinal degenerations, including but not limited to AMD.

The invention as disclosed herein should not be construed to be limited to AMD and/or oxidative stress-induced cell death. Oxidative stress is associated with a wide range of retinal degenerations, and oxidative stress has been shown to decrease photoreceptor survival human diseases, including age-related macular degeneration (AMD), atherosclerosis, Alzheimer's disease and others. Oxidative stress is a general mechanism in which cells and tissues undergo damage in high oxygen environments. Mechanisms will vary depending on disease process, but include mitochondrial damage and dysfunction, peroxide production, free radical formation, and other mechanisms. Without loss of generality, drugs that prevent or reverse effects of tissue damage from oxidative stress are useful for slowing or reversing the progression of human disease. Non-limiting examples of such diseases include: heart failure and other cardiovascular such as atherosclerosis; retinal degenerations such as age-related macular degeneration; pulmonary fibrosis; kidney (renal) disease; diabetic macular edema and retinopathies; neurodegenerations such as Alzheimer's disease; certain skeletal muscle disorders such as mitochondrial myopathy and Barth's syndrome; ocular disorders and diseases such as cataract and glaucoma; and Liver disease.

As described herein, exemplary compounds of the invention were found to mitigate risk of oxidative stress damage in tissue culture models of disease. For example, compounds 414 and 434 were shown to protect RPE cells (ARPE-19), neuronal cells (C6), and endothelial cells (HUVEC) from oxidative stress and are beneficial to treat diseases contemplated herein. In non-limiting embodiments, compound 414, compound 434, and ciclopirox enhance metabolic function such as adenosine triphosphate (ATP) production, basal respiration, maximal respiration, and spare respiration in RPE cells.

In one aspect, the invention provides a method of treating AMD in a subject, and/or an anterior segment ocular disorder (such as but not limited to Fuchs endothelial corneal dystrophy (FECD), cataracts, glaucoma, and/or keratoconus). In certain embodiments, the method comprises administering to the subject a pharmaceutical composition comprising an effective amount of a compound of formula (1):

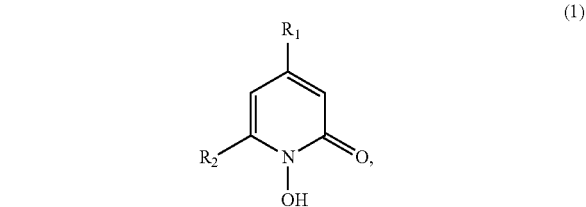

(1)

wherein $R_1$ is $C_1$-$C_3$ alkyl, $R_2$ is $C_1$-$C_{10}$ alkyl or $C_3$-$C_7$ cycloalkyl; or a pharmaceutically acceptable salt, solvate or prodrug thereof, and at least one pharmaceutically acceptable carrier. In various embodiments $R_1$ is methyl. In various embodiments, $R_2$ is substituted at anywhere on the cycloalkyl ring, by way of non-limiting example with $C_1$-$C_3$ alkyl, halogen, hydroxyl, and/or amine. In various embodiments, $R_2$ is cyclohexyl or 2,4,4-trimethyl-pent-1-yl. In certain embodiments, the compound of formula (1) is ciclopirox (also known as 6-cyclohexyl-1-hydroxy-4-methylpyridin-2 (1H)-one). In other embodiments, the compound is not ciclopirox. In yet other embodiments, the compound is piroctone (1-hydroxy-4-methyl-6-(2,4,4-trimethylpentyl)-2 (1H)-pyridone). In yet other embodiments, the compound is not piroctone.

A skilled person will recognize that in various embodiments it can be advantageous to incorporate the compound into the pharmaceutical composition as a salt. Various counterions will be desirable for when employing different formulations and methods of administration and all pharmaceutically acceptable salts are contemplated for use with the present invention. In various embodiments, the pharmaceutical composition is formulated for ocular administration. In various embodiments, the compound is ciclopirox olamine.

In another aspect, the invention provides a method of treating AMD in a subject, and/or an anterior segment ocular disorder (such as but not limited to Fuchs endothelial corneal dystrophy (FECD), cataracts, glaucoma, and/or keratoconus). In certain embodiments, the method comprises administering to the subject a pharmaceutical composition comprising an effective amount of a compound of formula (2):

(2)

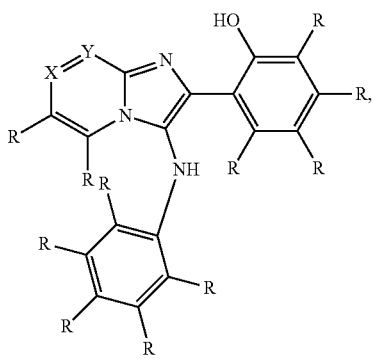

wherein one of X or Y is N and the other is CR, and each instance of R is independently selected from the group consisting of H, $C_1$-$C_3$ alkyl, and halogen; or a pharmaceutically acceptable salt, solvate or prodrug thereof, and at least one pharmaceutically acceptable carrier.

As indicated by X and Y in formula (3), in various embodiments the compound is an imidazopyrimidine or an imidazopyrazine. Accordingly, in various embodiments the compound is a compound of formula (3):

(3)

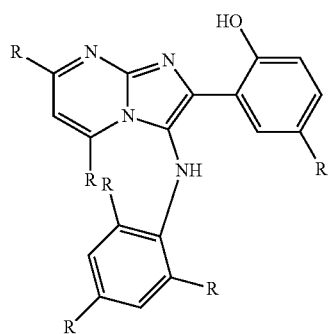

wherein each instance of R is independently selected from the group consisting of H, $C_1$-$C_3$ alkyl, and halogen; or a pharmaceutically acceptable salt, solvate or prodrug thereof.

In various embodiments, the compound is a compound of formula (4):

(4)

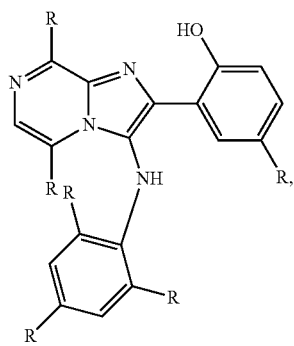

wherein each instance of R is independently selected from the group consisting of H, $C_1$-$C_3$ alkyl, and halogen; or a pharmaceutically acceptable salt, solvate or prodrug thereof.

In various embodiments, R is selected from the group consisting of Cl, Br, methyl, or ethyl.

In various embodiments, the compound of formula (2) is selected from the group consisting of:

(5)

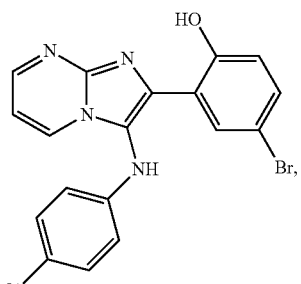

(6)

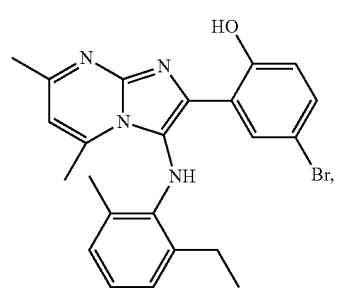

(7)

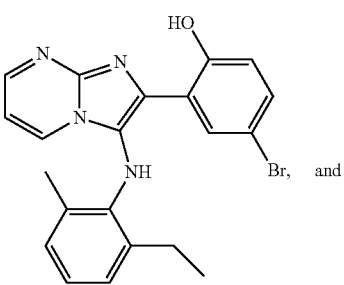

and (8)

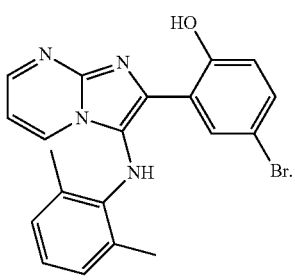

In another aspect, the invention provides a compound of formula (2):

(2)

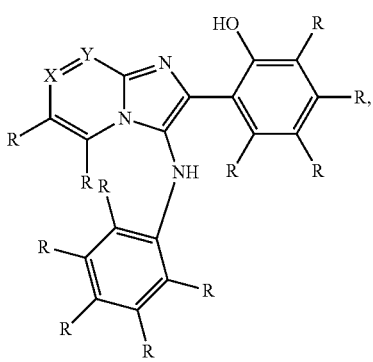

wherein one of X or Y is N and the other is CR, and each instance of R is independently selected from the group consisting of H, $C_1$-$C_3$ alkyl, and halogen; or a pharmaceutically acceptable salt, solvate or prodrug thereof, and at least one pharmaceutically acceptable carrier.

Despite advancements in the understanding of the pathophysiology of atrophic AMD, approved therapies remain elusive for this form of the disease. The atrophic or "dry" form of AMD is characterized loss of RPE cells with loss of photoreceptors and the choriocapillaris. While the etiology of the AMD is not fully understood, it is clear that risk factors such as advanced age, cigarette smoking, diet, and genetic differences (including but not limited to race) play a role in the development of the disease. RPE cells are susceptible to oxidative stress and factors such as intense illumination into the eye or toxins in cigarettes contribute to the cumulative damage caused by this process. Moreover, antioxidant capacity decreases and the efficiency of reparative systems become impaired. Age-related damage to Bruch's membrane (BM) caused by risk factors such as cigarette smoking is also associated with aberrant RPE cell behavior. These changes are a hallmark of AMD and result in retinal dysfunction and cell loss seen in atrophic AMD. The presence of hydrogen peroxide in RPE cells catalyze oxidation reactions and create ROS which cause irreversible damage to cells. As people age, the ability of these cells to protect against ROS is compromised. Given the observation that mitochondrial DNA damage and repair in RPE associated with aging and AMD, reducing oxidative stress is a viable therapeutic target. In certain embodiments, the compounds of the invention prevent or minimize cell death caused by any cellular assault, which includes oxidative stress-related cellular assault or any other forms of cellular assault.

Tert-butyl hydroperoxide (TBHP) exposure has been demonstrated to disrupt junctional integrity of the RPE and cause lipid peroxidation of the membrane bilayer as well as the oxidation of glutathione, endoplasmic reticulum $Ca^{2+}$ release, increased intracellular calcium ($[Ca^{2+}]$), and increased mitochondrial inner membrane permeability. UV-B light damage has been shown to target mitochondrial DNA damage and produce reactive oxygen species. Chronic nitric oxide production and subsequent nitrite exposure by cigarette smoking is a risk factor strongly associated with AMD. These changes contribute to the cumulative damage to the BM and result in the age-related collagen cross linking, a decline in collagen solubility, and subsequent membrane damage. In the examples below, treatment with one or more of the compounds of the invention promotes cell survival as measured by a cell viability assay when challenged with tert-butyl hydroperoxide, U-VB light, or on damaged extracellular matrix. Ciclopirox olamine improves mitochondrial function as well as downregulates expression of pro-apoptotic genes as measured by quantitative PCR when challenged with tert-butyl hydroperoxide in ARPE-19 cells. In human iPSC-derived RPE, ciclopirox olamine improved mitochondrial respiration rate in all parameters, including ATP production and maximal respiration. Without wishing to be limited by theory, this suggests that ciclopirox olamine can exhibit protective effects by enhancing mitochondrial respiration.

Imidazopyrimidine and imidazopyrazine also promote cell survival in RPE cells after challenge with tert-butyl hydroperoxide and UV-B light. These compounds also protect RPE cell survival on nitrite-modified extracellular matrix, an in vitro model of aged Bruch's membrane, and improve mitochondrial function after challenge with TBHP.

The observation that treatment with ciclopirox olamine and imidazopyrimidines, imidazopyrazines improves mitochondrial respiration in iPSC-derived RPE cells is intriguing given the potential use of these cells as an in vitro assay system for disease modeling, preclinical therapeutic and drug toxicity studies. One of the many advantages of using human iPSC derived from patients is that it allows the investigator to use patient-specific cell types that are not easily attainable. This technology also allows the investigator to study disease progression in patient-specific cells in which animal models are extremely limited, such as disease progression seen in AMD. iPSCs are also valuable given the potential variability between the human disease and animal model.

Accordingly, and again without wishing to be limited by theory, enhancing metabolic activity is a valid target for degenerative diseases such as AMD. The data presented in the below examples show that the compounds of the invention protect and enhance mitochondrial respiration in iPSC-derived RPE from a 71-year-old donor. Moreover, mitochondrial function improved in iPSC-derived RPE treated with ciclopirox olamine alone. These data along with the results of the gene expression assay in human ARPE-19 cells suggests that, in certain non-limiting embodiments, the method of the invention works by targeting the mitochondria and enhancing metabolic activity in RPE cells but a skilled person will appreciate that regardless of the precise mechanism the claimed methods are useful for the treatment of AMD.

The invention provides the following embodiments, which are non-limiting in scope:

Embodiment 1: A method of treating or preventing retinal degeneration in a subject, the method comprising administering to the subject a pharmaceutical composition comprising an effective amount of at least one selected from the group consisting of: (a) a compound of formula (1):

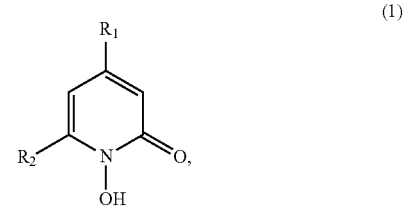

wherein $R_1$ is $C_1$-$C_3$ alkyl, $R_2$ is $C_1$-$C_{10}$ alkyl or $C_3$-$C_7$ cycloalkyl; and wherein the compound is not ciclopirox (6-cyclohexyl-1-hydroxy-4-methyl-2(1H)-pyridone); (b) a compound of formula (2):

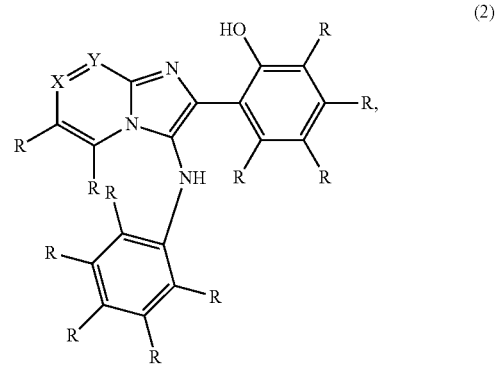

wherein one of X or Y is N and the other is CR; and wherein each instance of R is independently selected from the group consisting of H, $C_1$-$C_3$ alkyl, and halogen; or a salt, solvate, or prodrug thereof.

Embodiment 2: The method of Embodiment 1, wherein the retinal degeneration comprises age-related macular degeneration (AMD).

Embodiment 3: A method of treating or preventing an anterior segment ocular disorder, the method comprising administering to the subject a pharmaceutical composition comprising an effective amount of at least one selected from the group consisting of: (a) a compound of formula (1):

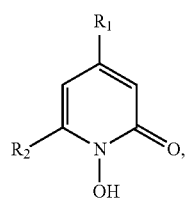

(1)

wherein $R_1$ is $C_1$-$C_3$ alkyl, $R_2$ is $C_1$-$C_{10}$ alkyl or $C_3$-$C_7$ cycloalkyl; and wherein the compound is not ciclopirox (6-cyclohexyl-1-hydroxy-4-methyl-2(1H)-pyridone); (b) a compound of formula (2):

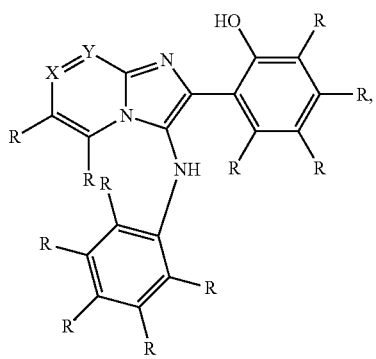

(2)

wherein one of X or Y is N and the other is CR; and wherein each instance of R is independently selected from the group consisting of H, $C_1$-$C_3$ alkyl, and halogen; or a salt, solvate, or prodrug thereof.

Embodiment 4: The method of Embodiment 3, wherein the disorder comprises at least one selected from the group consisting of Fuchs Endothelial Corneal Dystrophy, cataracts, glaucoma, and keratoconus.

Embodiment 5: The method of any of Embodiments 1-4, in (1) $R_1$ is methyl.

Embodiment 6: The method of any of Embodiments 1-4, wherein in (1) $R_2$ is cyclohexyl or 2,4,4-trimethyl-pent-1-yl.

Embodiment 7: The method of any of Embodiments 1-4, wherein the compound of formula (1) is piroctone (1-hydroxy-4-methyl-6-(2,4,4-trimethylpentyl)-2(1H)-pyridone).

Embodiment 8: The method of any of Embodiments 1-4, wherein the compound of formula (2) is a compound of formula (3):

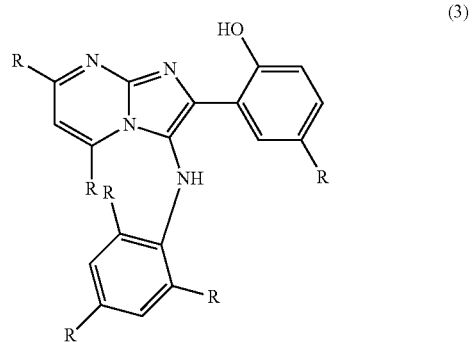

(3)

wherein each instance of R is independently selected from the group consisting of H, $C_1$-$C_3$ alkyl, and halogen.

Embodiment 9: The method of any of Embodiments 1-4, wherein the compound of formula (2) is a compound of formula (4):

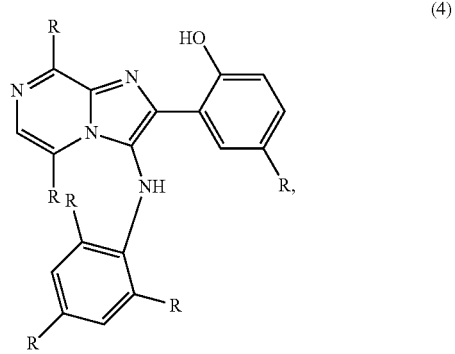

(4)

wherein each instance of R is independently selected from the group consisting of H, $C_1$-$C_3$ alkyl, and halogen.

Embodiment 10: The method of any of Embodiments 1-4, wherein the compound of formula (2) is selected from the group consisting of:

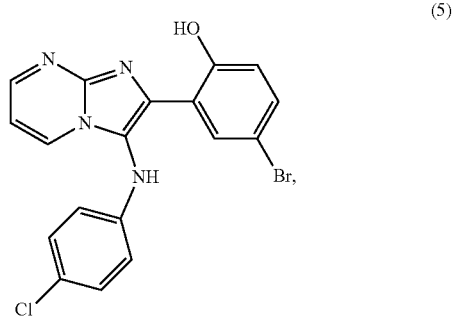

(5)

(6)

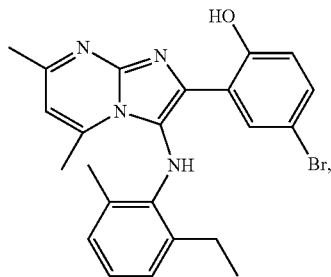

(7)

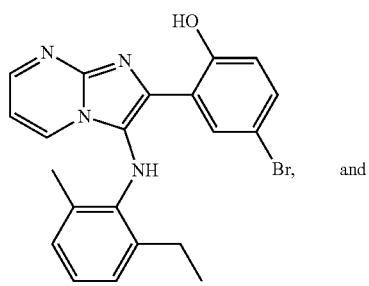
and (8)

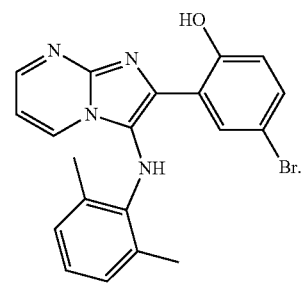

Embodiment 11: The method of any one of Embodiments 1-10, wherein the pharmaceutical composition is formulated for ocular administration.

Embodiment 12: A method of treating, ameliorating, or preventing cell death, or promoting cell viability, in a subject, the method comprising administering to the subject a pharmaceutical composition comprising an effective amount of at least one selected from the group consisting of:
(a) a compound of formula (1):

(1)

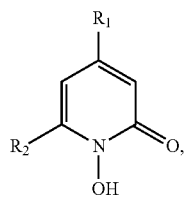

wherein $R_1$ is $C_1$-$C_3$ alkyl, $R_2$ is $C_1$-$C_{10}$ alkyl or $C_3$-$C_7$ cycloalkyl; (b) a compound of formula (2):

(2)

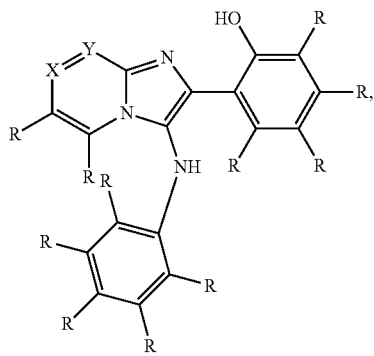

wherein one of X or Y is N and the other is CR, and wherein each instance of R is independently selected from the group consisting of H, $C_1$-$C_3$ alkyl, and halogen; or a salt, solvate, or prodrug thereof.

Embodiment 13: The method of Embodiment 12, wherein the cell death comprises oxidative stress-induced cell death.

Embodiment 14: The method of Embodiment 12, wherein the cell comprises a lens epithelial cell.

Embodiment 15: The method of Embodiment 12, wherein the cell death is associated with at least one disease selected from the group consisting of heart failure and other cardiovascular; pulmonary fibrosis; kidney disease; diabetic macular edema and retinopathies; neurodegeneration; mitochondrial myopathy; Barth's syndrome; and liver disease.

Embodiment 16: The method of Embodiment 12, wherein in (1) $R_1$ is methyl.

Embodiment 17: The method of Embodiment 12, wherein in (1) $R_2$ is cyclohexyl or 2,4,4-trimethyl-pent-1-yl.

Embodiment 18: The method of Embodiment 12, wherein the compound of formula (1) is ciclopirox or piroctone.

Embodiment 19: The method of Embodiment 12, wherein the compound of formula (2) is a compound of formula (3):

(3)

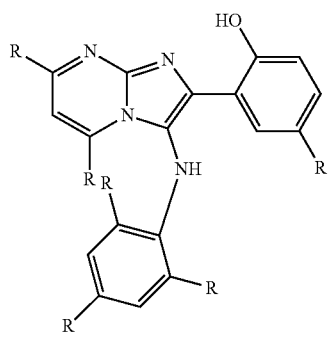

wherein each instance of R is independently selected from the group consisting of H, $C_1$-$C_3$ alkyl, and halogen.

Embodiment 20: The method of Embodiment 12, wherein the compound of formula (2) is a compound of formula (4):

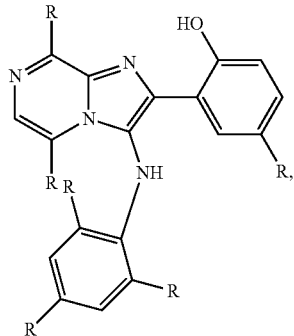

(4)

wherein each instance of R is independently selected from the group consisting of H, $C_1$-$C_3$ alkyl, and halogen.

Embodiment 21: The method of Embodiment 12, wherein the compound of formula (2) is selected from the groin consisting of:

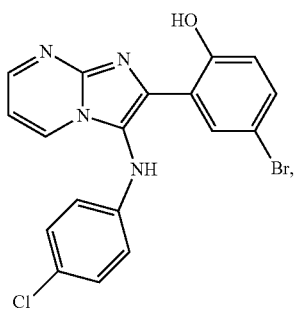

(5)

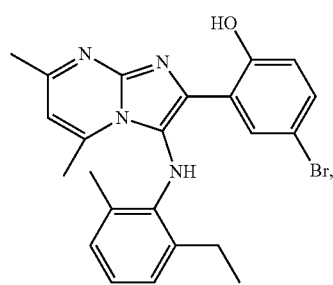

(6)

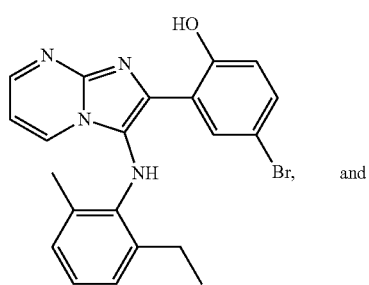

(7)

and

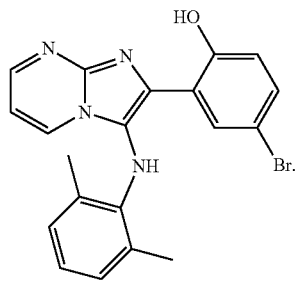

(8)

Embodiment 22: A compound of formula (2):

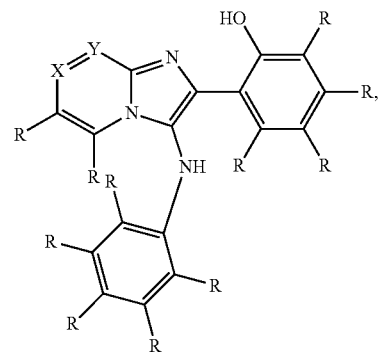

(2)

wherein one of X or Y is N and the other is CR, and wherein each instance of R is independently selected from the group consisting of H, $C_1$-$C_3$ alkyl, and halogen, or a salt, solvate, or prodrug thereof.

Embodiment 23: The compound of Embodiment 22, which is a compound of formula (3):

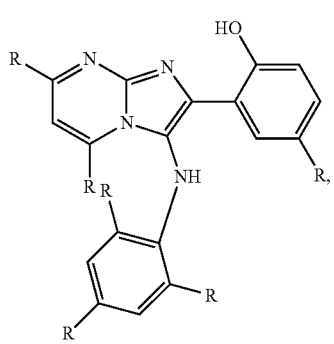

(3)

wherein each instance of R is independently selected from the group consisting of H, $C_1$-$C_3$ alkyl, and halogen.

Embodiment 24: The compound of Embodiment 22, which is a compound of formula (4):

(4)

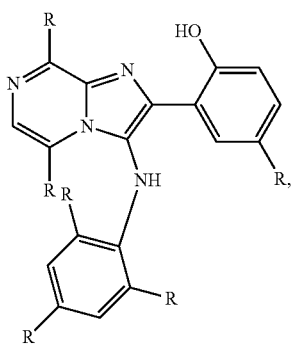

wherein each instance of R is independently selected from the group consisting of H, $C_1$-$C_3$ alkyl, and halogen.

Embodiment 25: The compound of Embodiment 22, which is selected from the group consisting of:

(5)

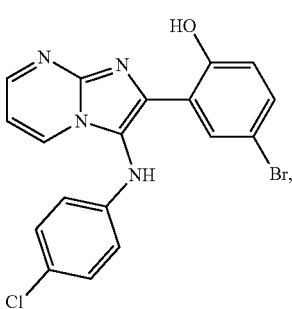

(6)

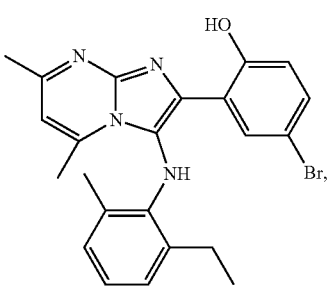

(7)

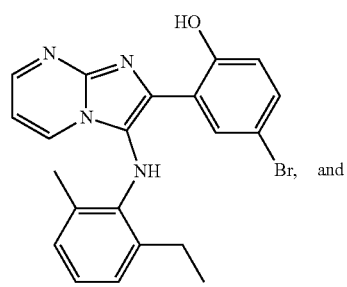
and (8)

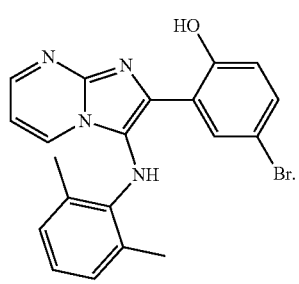

Embodiment 26: A pharmaceutical composition comprising the compound of any one of Embodiments 22-25 and at least one pharmaceutically acceptable excipient.

Embodiment 27: The pharmaceutical composition of Embodiment 26, which is formulated for ocular administration.

Embodiment 28: The pharmaceutical composition of Embodiment 27, which comprises gamma cyclodextrin (γ-cyclodextrin) and/or hydroxypropyl-beta-cyclodextrin (HPBCD).

Embodiment 29: The pharmaceutical composition of any of Embodiments 26-28, which has pH of about 5-8.

Embodiment 30: The pharmaceutical composition of any of Embodiments 26-29, which is lyophilized.

Embodiment 31: The pharmaceutical composition of any of Embodiments 26-29, which further comprises a thickening agent.

Administration/Dosage/Formulations

The regimen of administration may affect what constitutes an effective amount. The therapeutic formulations may be administered to the subject either prior to or after the onset of a AMD. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat disease in the patient. An effective amount of the therapeutic compound necessary to achieve a therapeutic effect may vary according to factors such as the state of the disease or disorder in the patient; the age, sex, and weight of the patient; and the ability of the therapeutic compound to treat AMD in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a AMD in a patient.

The carrier may be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, once every two weeks, once every three weeks, once per month, once every 2 months, once every 3 months, and/or once every 1-12 weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments thereinbetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the compounds of the invention can be administered ophthalmically, for example via intraocular or periocular injection. In other embodiments, the compounds are administered in a gel or a pegylated material. In other embodiments, the compounds themselves are pegylated or conjugated to a long-lasting biological molecule. In yet other embodiments, the compounds are formulated for slow delivery to the eye, for example using contact lenses comprising a polymer that releases the drug slowly, using punctual plugs, and/or using any delivery methodology that is known in the art and compatible with the present compounds.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a AMD in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastric, intrathecal, subcutaneous, intramuscular, intradermal, intra-arterial, intravenous, intrabronchial, inhalation, topical administration, and ophthalmic(including but not limited to topical, subconjunctival, subTenon's, suprachoroidal, intravitreal, or subretinal), Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically acceptable excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The present invention also includes a multi-layer tablet comprising a layer providing for the delayed release of one or more compounds of the invention, and a further layer providing for the immediate release of a medication for treatment of certain diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Ophthalmological Administrations

The invention contemplates administering to the eye the compounds useful within the invention. Any ophthalmological formulations can be useful within the present invention, as well as they allow for application of the compounds useful within the invention to the eye.

In certain embodiments, the compositions of the invention comprise a cyclodextrin, which is a cyclic oligosaccharide comprising a macrocyclic ring of glucose subunits joined by α-1,4-glycosidic bonds. In certain embodiments, the cyclodextrin comprises α (alpha)-cyclodextrin (6 glucose subunits). In certain embodiments, the cyclodextrin comprises β (beta)-cyclodextrin (7 glucose subunits). In certain embodiments, the cyclodextrin comprises γ (gamma)-cyclodextrin (8 glucose subunits). In certain embodiments, the cyclodextrin comprises methyl-α-cyclodextrin. In certain embodiments, the cyclodextrin comprises methyl-β-cyclodextrin. In certain embodiments, the cyclodextrin comprises methyl-γ-cyclodextrin. In certain embodiments, the cyclodextrin comprises hydroxypropyl-α-cyclodextrin. In certain embodiments, the cyclodextrin comprises hydroxypropyl-β-cyclodextrin. In certain embodiments, the cyclodextrin comprises hydroxypropyl-γ-cyclodextrin.

In a non-limiting example, the compositions of the invention comprise gamma cyclodextrin (or γ-cyclodextrin). A solution of gamma cyclodextrin can be prepared in water at concentrations up to its solubility limit of about 23.2 mg/mL. The pH of this cyclodextrin solution can then be adjusted to a pH at which the active compound is most soluble. The active compound is then added so that the molar ratio of gamma cyclodextrin to active compound is anywhere from about 1:1 to about 10:1. The resulting suspension or solution can then be stirred for a period of time (for example, 1 hour) after which the pH is adjusted to about 5-8, preferably about 6.5-7.5. The suspension or solution can be allowed to stir for up to about 24 hours after which it is used directly, diluted with buffer to a desired concentration, and/or lyophilized to provide a powder for reconstitution. The lyophilized powder can be suspended in an amount of water that will not dissolve the powder completely but will provide a fine suspension. This suspension can then be further formulated with a thickening agent to improve adherence to the eye. Thickening agents include, but are not limited to, carboxymethylcellulose (for example, at a concentration of about 0.05-5%), or other approved agents.

A non-limiting example of ciclopirox formulation in cyclodextrin follows. Gamma cyclodextrin (232 mg) was dissolved in 1 mL water, and the pH adjusted to about 8.0 to give a solution of 0.178 M gamma cyclodextrin. Ciclopirox was added (6.39 mg) and the suspension was stirred for 1-24 hours. Higher amounts of ciclopirox can be used, up to 30 mg for a 1:1 complex. The pH was then adjusted to about 6.5-7.5, and the solution or suspension lyophilized. The lyophilized powder was suspended in an amount of water which did not fully dissolve the material but provided a fine suspension. Carboxymethylcellulose can be added to provide greater adherence to the eye at about 0.05-5% concentrations and to keep the particles suspended for direct application to the eye.

In a non-limiting example, the compositions of the invention comprise hydroxypropyl beta cyclodextrin (HPBCD). A non-limiting example of ciclopirox formulation in HPBCD follows. 2.00 g HPBCD was dissolved in 4 mL deionized and filtered water by slow inversion/rotation. After an hour of slow inversion, the solid had dissolved to provide a clear solution. The volume was adjusted to 5.00 mL to provide 5.00 mL of a 40% clear solution by weight. To the 5.00 mL solution of 40% HPBCD was added 175 mg ciclopirox powder, and the vial was sealed and placed under slow rotary inversion to dissolve the solid. After 1 hour mixing the ciclopirox had completely dissolved to give a solution of 35 mg/mL ciclopirox in 40% HPBCD. In contrast, the solubility of ciclopirox in pH 7.4 phosphate buffer (no saline) is 1.0 mg/mL. This 35 mg/mL solution was easily filtered through a 0.22 um syringe filter (MILLEX GV, PVDF membrane). The filtered solution was then checked for pH and a high value of approx. 8.3 was noted, and the pH adjusted under stirring to 7.4 by the addition of a total of 0.5 mL 1M HCl. The pH 7.4 adjusted solution of 35 mg/mL ciclopirox in 40% HPBCD (osmolarity 0.670) was diluted incrementally with deionized water until the osmolarity was 0.376 with a resulting concentration of 21.3 mg/mL. The total volume of 175 mg ciclopirox was thus prepared at 21.3 mg/mL in 8.2 mL volume. Since the addition of water was necessary to reduce the osmolarity, the concentration of HPBCD was therefore now 24%. 21.3 mg/mL ciclopirox in 24% HPBCD, total volume of 8.2 mL, was partitioned into 1 mL sample vials. The solution may be frozen at −80° C. and thawed at room temperature.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of AMD in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in practicing the following examples are here described:

Human Retinal Pigment Epithelial (RPE) Cell Culture

Immortalized human RPE cells (ARPE-19) obtained from the American Type Culture Collection (ATCC, Manassas, Va., USA) were cultured in Dulbecco's modified Eagle's medium (DMEM; Thermo Fisher Scientific, Waltham, Mass.) containing 10% fetal bovine serum (FBS), 100 IU/mL penicillin, 100 µg/mL streptomycin, 100 µg/mL gentamicin, and 2.5 µg/mL amphotericin B (Thermo Fisher Scientific).

Human Induced Pluripotent Stem Cell (IPSC) Culture

Human iPSCs were derived from fibroblasts of a 71-year-old female donor with no history of retinal disease. A skin specimen was processed as previously described. Briefly, the skin biopsy was transplanted onto a culture plate and fibroblasts were grown to confluence and then treated with four Yamanaka factors, Oct3/4, Sox-2, Klf4, and c-Myc using the CytoTune™-iPS 2.0 Sendai Reprogramming Kit according to the manufacturer's instructions (Invitrogen-Gibco, Life Technologies=) (31-36). Newly generated iPSC colonies were purified and expanded using MTeSR1™ media (Stem Cell Technologies, Vancouver, Canada).

Generation of Human IPSC-Derived RPE

Human iPSCs were differentiated to iPSC-derived RPE cells as previously described. Human iPSC colonies were lifted and grown as embryoid bodies (EBs) for 4 days in EB formation medium (STEMCELL Technologies). After 5 days, EB medium was replaced with neural induction medium (NIM) containing DMEM/F12 (1:1), 1% N-2 supplement (MEM non-essential amino acids and 2 µg/mL heparin) and suspended EB aggregates were plated onto laminin-coated culture plates and allowed to reattach. After 16 days, neural induction medium was replaced with retinal differentiation medium (RDM) containing DMEM/F12 (3:1), 2% B-27 supplement (Invitrogen-Gibco, Life Technologies), MEM non-essential amino acids and penicillin/streptomycin. The adherent culture was maintained in RDM until the appearance of pigmented iPSC-derived RPE cells. Patches of pigmented iPSC-derived RPE cells were then micro-dissected and cultured on Transwell® plates with RDM+10% fetal bovine serum (FBS) for 2 days and then switched to RDM with 2% FBS until the cells were confluent. Human iPSC-derived RPE cells were then maintained in RDM and allowed to form monolayers within 90 days.

Induction of Oxidative Stress Using Tert-Butyl Hydroperoxide

Human ARPE-19 cells were plated in 96-well plates for 24 hours in DMEM supplemented with FBS and antibiotics. ARPE-19 cells were preincubated with either ciclopirox olamine (Sigma), compound 414 (Chemical Diversity, San Diego, Calif.), compound 434 (Chemical Diversity) or no compound for 24 hours and then exposed to varying concentrations of tert-butyl hydroperoxide (TBHP; Sigma-Aldrich, St. Louis, Mo.) the next day for 24 hours. Cell viability was measured the following day by RealTime-Glo™ MT cell viability assay (Promega, Madison, Wis.) using a BioTek FLx800™ fluorescence reader (BioTek, Winooski, Vt.).

Light Microscopy

Human ARPE-19 cells morphology was examined using phase contrast on a Zeiss 510 NLO confocal laser scanning microscope with a Plan-Apochromatic 20×0.8 DIC objective.

Induction of Oxidative Stress Using UV-B Light Damage

Human ARPE-19 cells were plated in 96-well plates for 24 hours in DMEM supplemented with FBS and antibiotics. ARPE-19 cells were preincubated with compound or no compound for 24 hours and then exposed to 1200 mJ/cm$^2$ ultraviolet B (UV-B) radiation in a chamber. Cell viability was measured the following day by ROS-Glo™ MT cell viability assay (Promega) using a BioTek FLx800™ fluorescence reader (BioTek, Winooski, Vt.).

Cytotoxicity Assay

Human ARPE-19 or primary RPE were plated in 96-well plates for 24 hours in DMEM supplemented with FBS and antibiotics. ARPE-19 cells were incubated with compound (Chemical Diversity) or exposed to tert-butyl hydroperoxide (Sigma-Aldrich, St. Louis, Mo.) for 24 hours. Cell cytotoxicity was measured the following day by CellTox™ Green cytotoxicity assay (Promega, Madison, Wis.) using a BioTek FLx800™ fluorescence reader (BioTek, Winooski, Vt.).

Measurement of Mitochondrial Respiration

Analysis of mitochondrial function was performed on live cells using XFe96 Extracellular Flux Analyzer (Seahorse Bioscience) using the cell mito stress test (CMST). Human ARPE-19 cells or iPSC-derived RPE were seeded in a 96 well plate and grown for 24 h. Cells were preincubated with compound or no compound for 24 hours and then exposed to varying concentrations of TBHP the next day for 24 hours. Cells were the washed with CMST assay medium (XF base medium DMEM supplemented with 2 mM glutamine, 5.5 mM glucose, and 1 mM sodium pyruvate, pH 7.4), and then incubated in CMST medium for 1 h at 37° C. in a non-CO2 incubator. The CMST assay protocol was performed by manufacturer guidance (Seahorse Bioscience). Oxygen consumption rate (OCR) was detected under basal conditions followed by the sequential addition of oligomycin, carbonyl cyanide 4-(trifluoromethoxy) phenylhydrazone (FCCP), as well as rotenone and antimycin A. The measured parameters include: basal respiration, adenosine triphosphate (ATP) production, maximal respiration, spare respiratory capacity.

Preparation of Extracellular Matrix (ECM)

To prepare the RPE ECM nitrite-treated plates, ARPE-19 cells were grown on 24-well Transwell permeable supports (Corning, Tewksbury, Mass., USA) in 12-well plates for 6 to 8 weeks to allow for ECM formation. ARPE-19 cells were removed by the addition of 20 mM ammonium hydroxide buffer for 20 minutes, and the ECM was washed three times with phosphate-buffered saline (PBS). Phosphate-buffered saline was removed from the RPE-derived ECM (RPE-ECM), which was then allowed to dry. The RPE-derived ECM plates were either used immediately after drying, or stored at −20° C. for future use. RPE-derived ECM was processed further to create four experimental plating surfaces (untreated, nitrite modified, nitrite modified followed by washing, or nitrite modified followed by washing and coating with a mixture of ECM ligands).

Nitrite Modification

Nitrite-modified ECM was prepared by adding 100 mM sodium nitrite to the ECM and incubating at 37° C. for 7 days. Plates were then washed at least four times with PBS and further incubated with PBS for 4 hours. Following this, the plates were washed at least two additional times to completely remove the nitrite.

Statistical Analysis

All experiments were conducted at least three times with triplicates. Independent, two-tailed t tests were performed using Prism (GraphPad Software, Inc., La Jolla, Calif.). A criterion of $\alpha=0.05$ was adopted.

Example 1: Ciclopirox Olamine Protects RPE Cells from Oxidative Damage

Initial screening of a library with 640 FDA-approved drugs (Enzo Life Sciences FDA-approved drug library) with known bioactivity, safety & bioavailability, and natural products was performed using TBHP, a chemical oxidizing agent, as a model of oxidative stress-induced cell death. Ciclopirox olamine was identified as a compound that significantly protects ARPE-19 cells from TBHP-induced cell death and this model was used to explore the protective mechanisms of ciclopirox olamine on human RPE cells.

After exposure to TBHP for 24 hours, treatment with ciclopirox olamine protects ARPE-19 cells from oxidative stress-induced cell death (FIG. 1A). Treatment with ciclopirox olamine also helps to preserve a normal morphology after challenge with TBHP (FIG. 1E).

Figure 2:
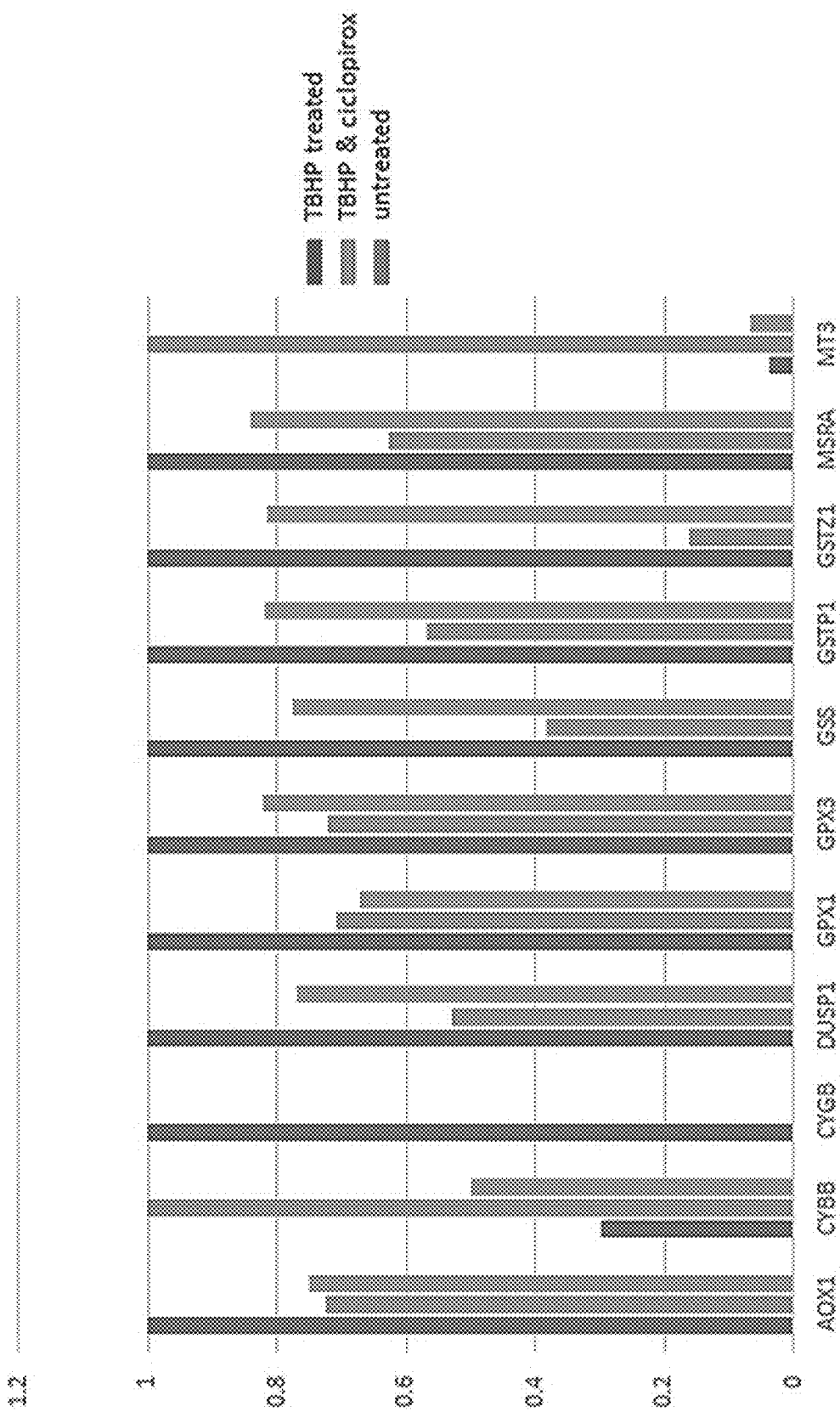
FIG. 2 depicts the gene expression pattern of oxidative stress related genes after tert-butyl hydroperoxide-induced cell death. Human ARPE-19 cells were preincubated ciclopirox olamine (0.9 µM) for 24 hours and then exposed to 300 µM tert-butyl hydroperoxide (TBHP) for 24 hours. Treatment with ciclopirox olamine results in a change in expression pattern in genes associated with anti-oxidative stress.
Figure 3:
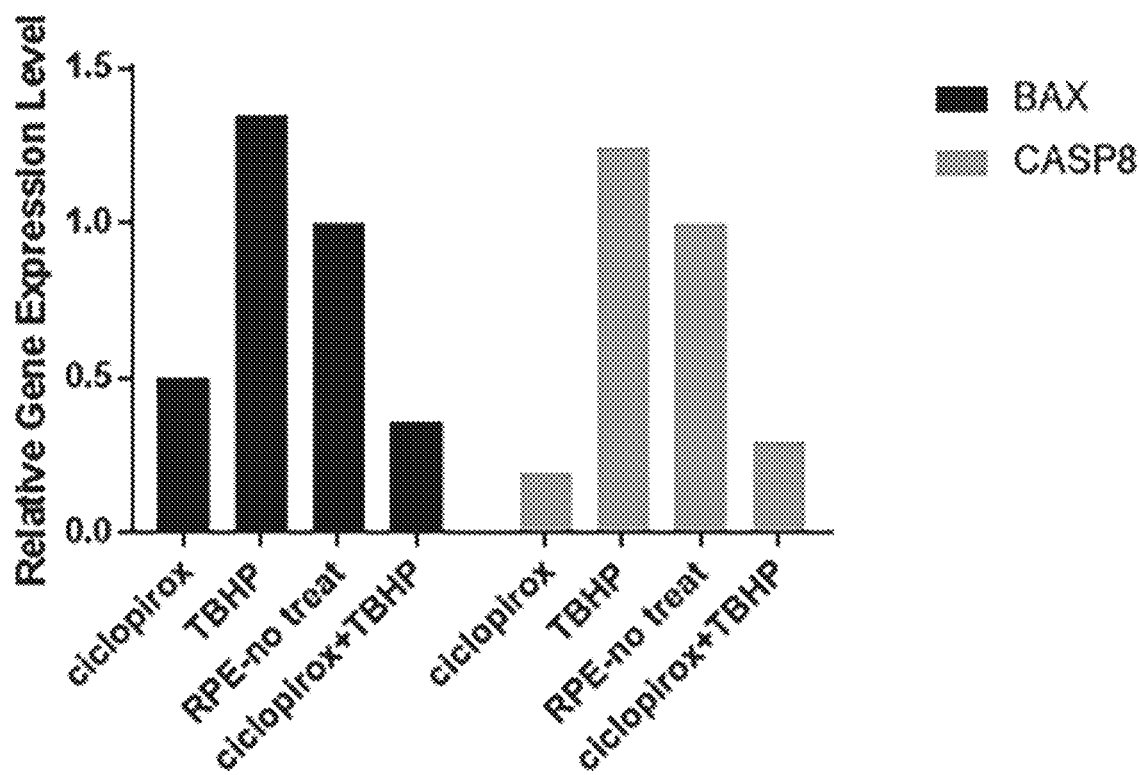
FIG. 3 depicts apoptotic gene expression patterns after oxidative stress-induced cell death in human retinal pigment epithelial (RPE) cells. Human ARPE-19 cells were preincubated with ciclopirox olamine for 24 hours and then exposed to 300 µM tert-butyl hydroperoxide (TBHP) for 24 hours. Treatment with ciclopirox olamine (0.9 µM) decreases expression of pro-apoptotic genes after tert-butyl hydroperoxide-induced cell death.
Figure 4B:
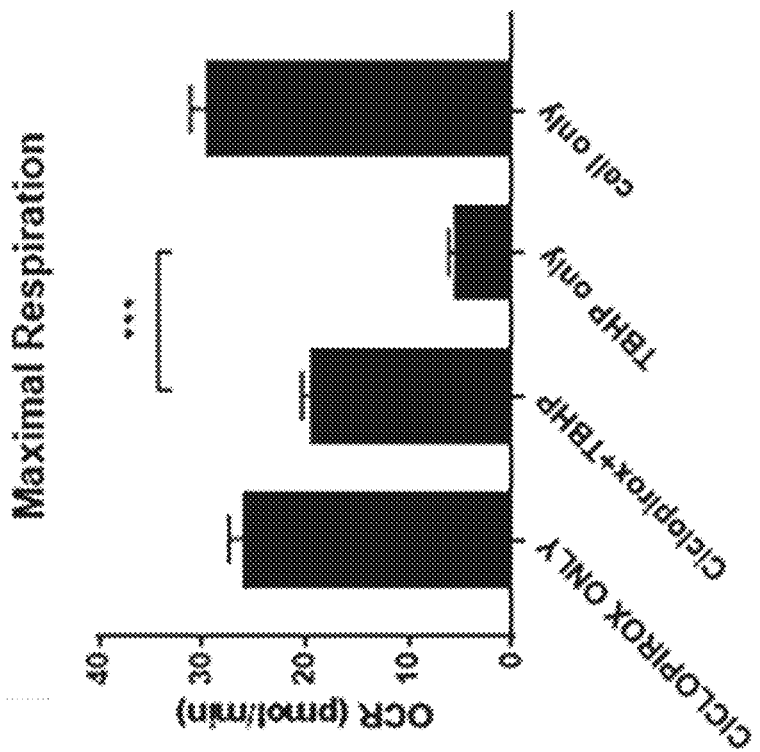
FIGS. 4A-4D indicate that ciclopirox olamine improves mitochondrial function after oxidative stress-induced cell death in human retinal pigment epithelial (RPE) cells. Human ARPE-19 cells were preincubated with 3 µM ciclopirox olamine for 18 hours, and then treated with 500 µM tert-butyl hydroperoxide (TBHP) for 24 hours. Oxygen consumption rate (OCR) was determined using the Seahorse XF analyzer to measure mitochondrial function.
Figure 4A:
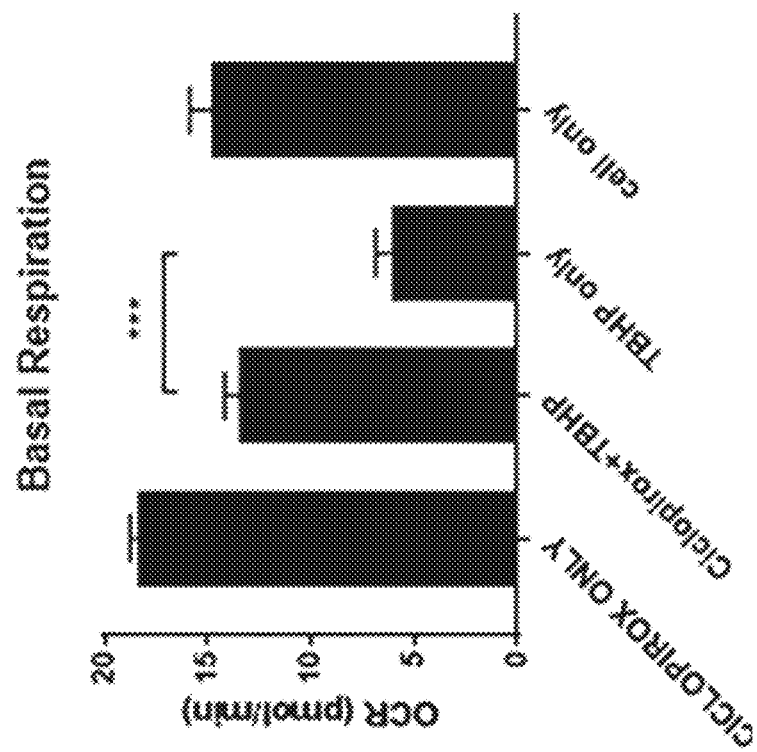
Figure 4D:
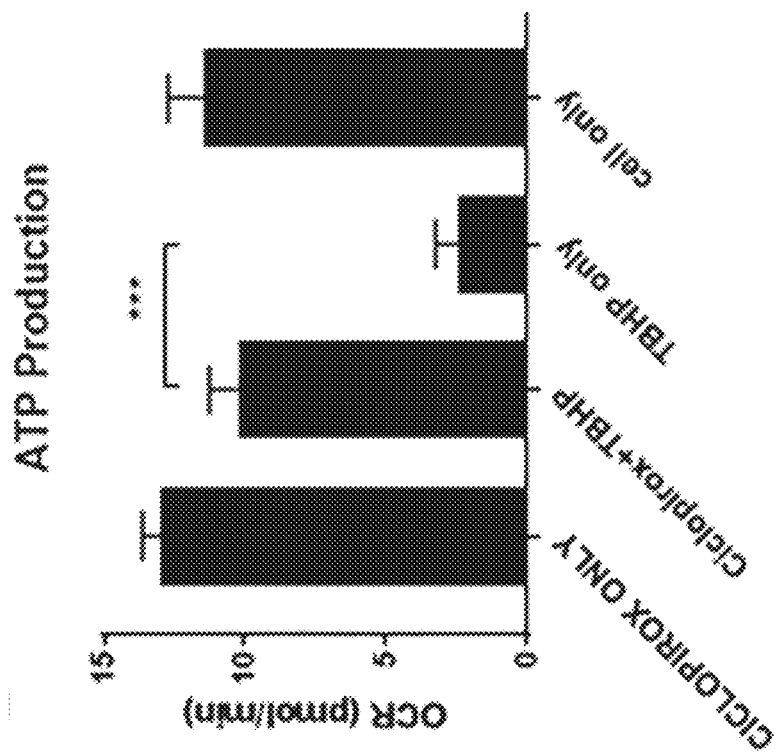
Figure 4C:
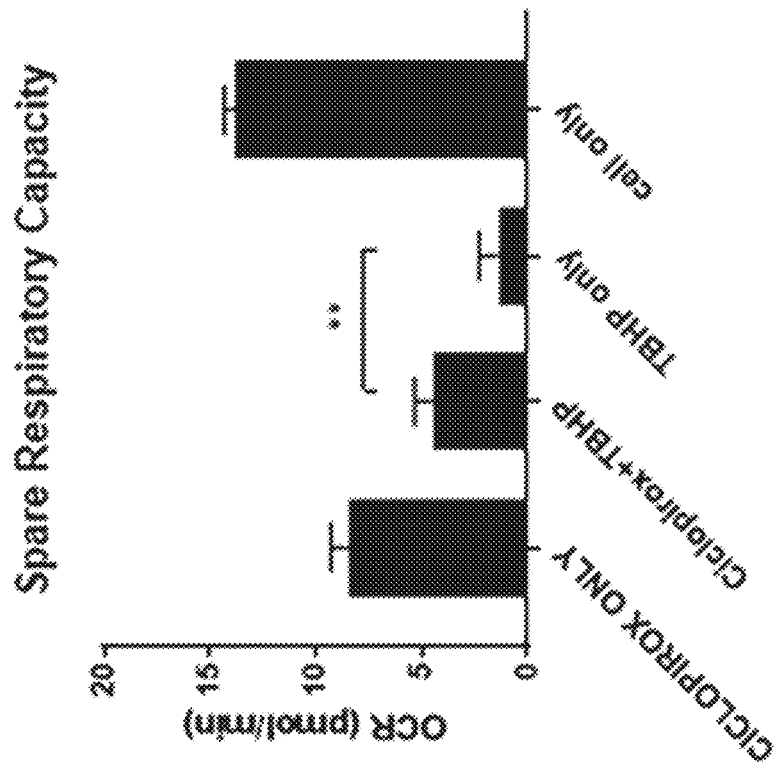

Example 2: Expression of Genes Related to Oxidative Stress and Apoptosis after Oxidative Damage The expression levels of genes related to oxidative stress were identified after exposure to TBHP for 24 hours (FIG. 2). Exposure to TBHP enhanced genes related to oxidative stress. After treatment with ciclopirox olamine these genes were reduced while genes related to anti-oxidative stress were elevated The expression level of genes related to apoptosis after exposure to TBHP for 24 hours was investigated. Genes of note that were observed to be upregulated after exposure to TBHP in the ARPE-19 cells were BCL2 associated X, apoptosis regulator (Bax) and caspase 8, both implicated in the initiation of apoptotic cell death. After treatment with ciclopirox olamine, gene expression of both Bax and caspase 8 were reduced (FIG. 3).

Example 3: Ciclopirox Olamine Improves Mitochondrial Function after Oxidative Stress-Induced Cell Death in Human RPE Cells Given the protective effects of ciclopirox on oxidative damage in other cell types such as liver and astrocytes, the effects of compound treatment on mitochondrial function in human RPE cells were investigated. Human ARPE-19 cells were preincubated with 3 µM ciclopirox olamine for 18 hours, then treated with 500 µM TBHP for 24 hours and oxygen consumption rate determined using the Seahorse XF analyzer. Treatment with ciclopirox olamine significantly increased basal respiration, maximal OCR, reserve capacity, and ATP turnover after challenge with TBHP (FIG. 4A-D).

Figure 5:
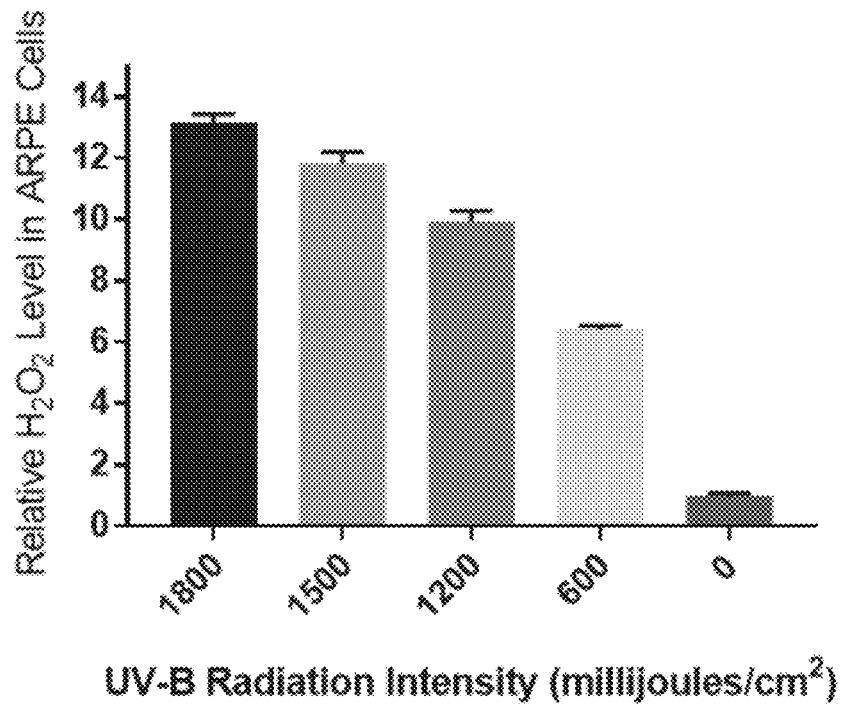
FIG. 5 shows various ultraviolet-B (UV-B) radiation causes increases in reactive oxygen species (ROS) production in RPE cells. Human ARPE-19 cells were cultured in complete DMEM for 24 hours and then exposed to various doses of UV-B radiation. These data show that UV-B light can be used to create oxidative stress in RPE cells.
Figure 6:
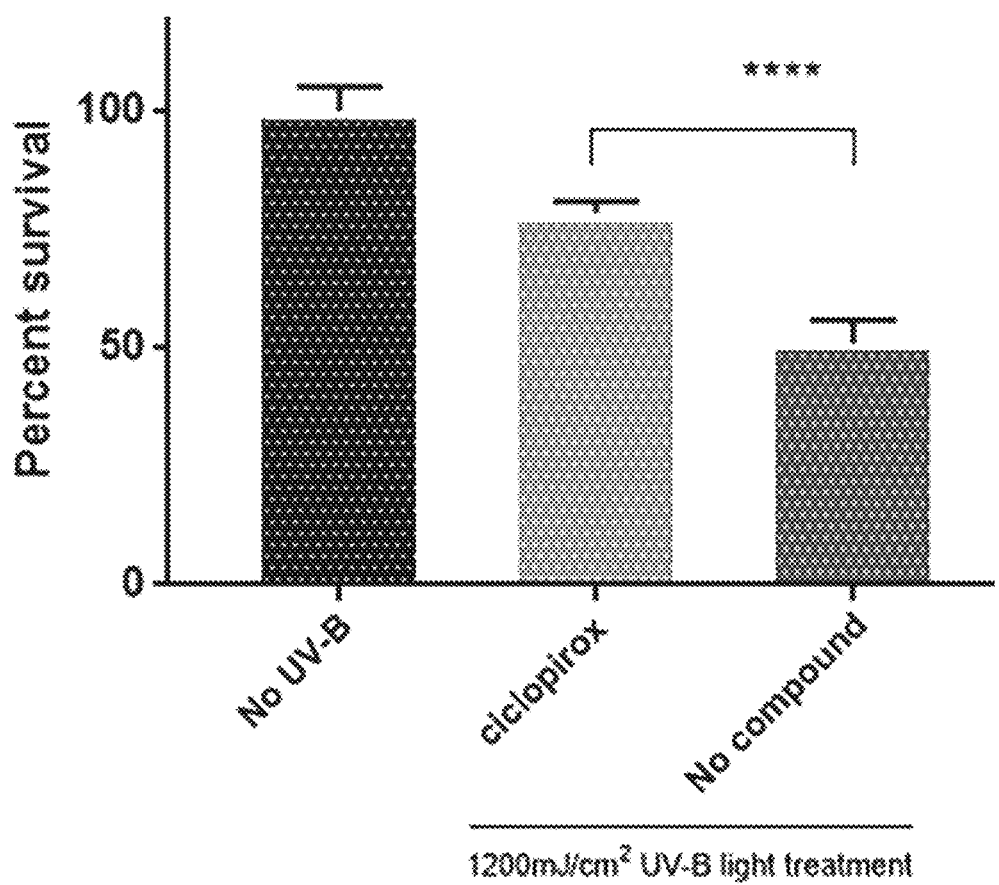
FIG. 6 shows that ciclopirox olamine protects human retinal pigment epithelial (RPE) cells from UV-B radiation damage. Human ARPE-19 cells were preincubated with 3 µM of ciclopirox olamine for 24 hours and then exposed to UV-B radiation (1200 mJ/cm$^2$). Protective effect of ciclopirox olamine on ARPE-19 cells exposed to UV-B radiation (1200 mJ/cm$^2$). ****P<0.0001

Example 4: Ciclopirox Olamine Protects RPE Cells from Light-Induced Oxidative Damage To confirm these results using TBHP, another model of oxidative stress in which human RPE cells are exposed to UV-B light was employed. FIG. 5 shows the generation of ROS at varying doses of UV-B radiation exposure in RPE cells. Human ARPE-19 cells were then preincubated with 3 µM of ciclopirox olamine for 24 hours and then exposed to 1200 mJ/cm$^2$ of UV-B radiation. Ciclopirox olamine protects human ARPE-19 cells exposed to 1200 mJ/cm$^2$ UV-B radiation (FIG. 6).

Figure 7A:
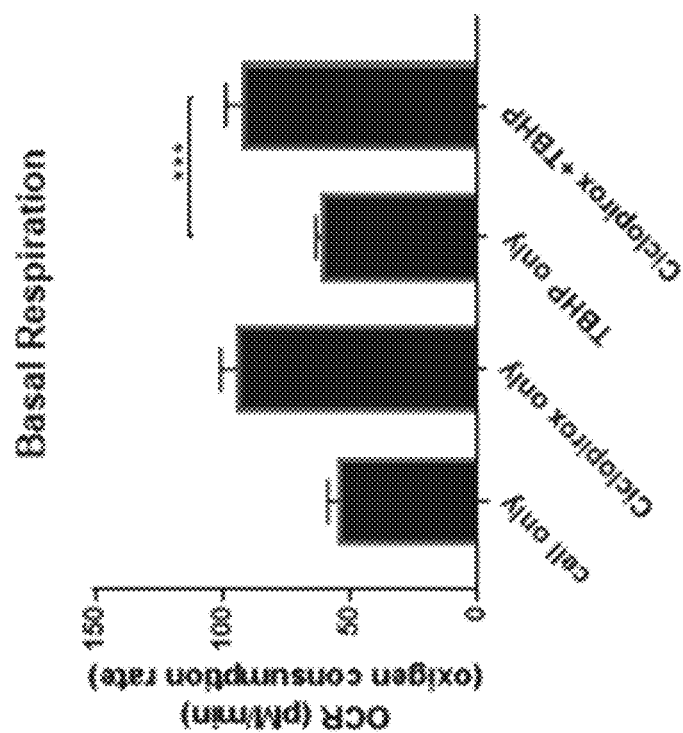
FIGS. 7A-7D show that ciclopirox olamine improves mitochondrial function in human induced pluripotent stem cell-derived RPE (iPSC-derived RPE) cells after oxidative stress-induced cells death. Human iPSC-derived RPE cells were preincubated with 3 μM ciclopirox olamine for 18 hours, then treated with 500 μM tert-butyl hydroperoxide (TBHP) for 24 hours. Oxygen consumption rate was determined using the Seahorse XF analyzer to measure mitochondrial function.
Figure 7B:
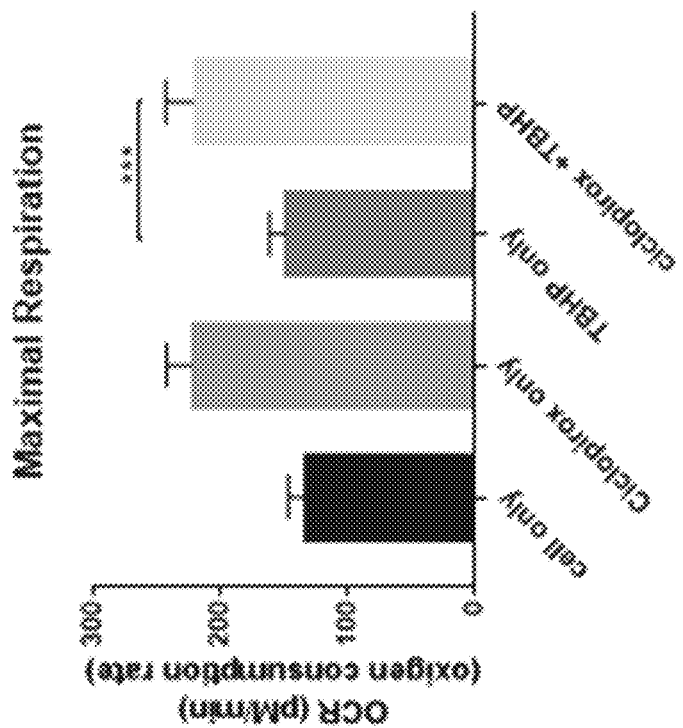
Figure 7D:
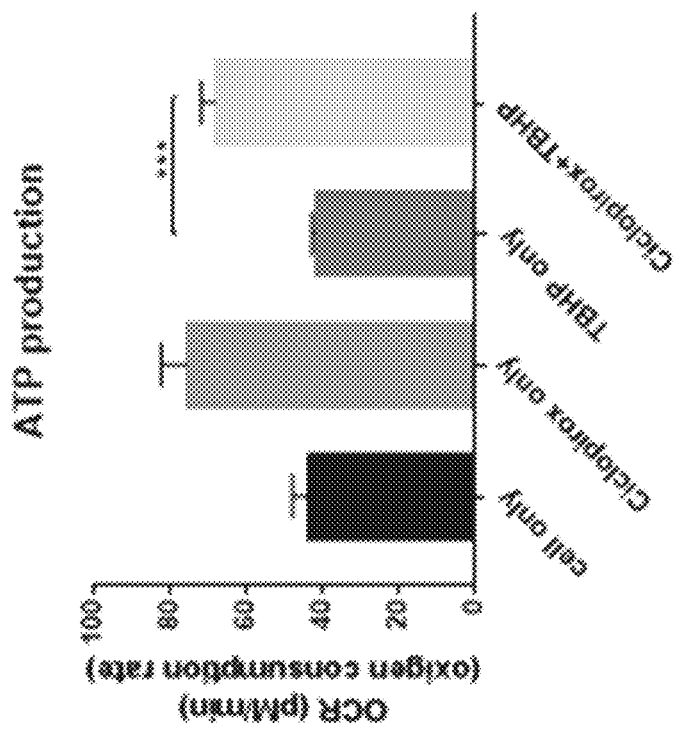
Figure 7C:
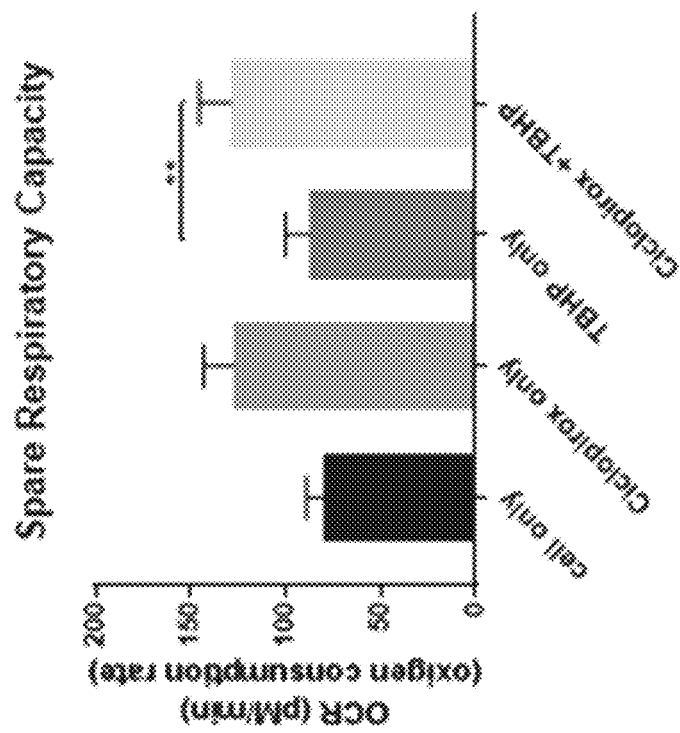
Figure 9A:
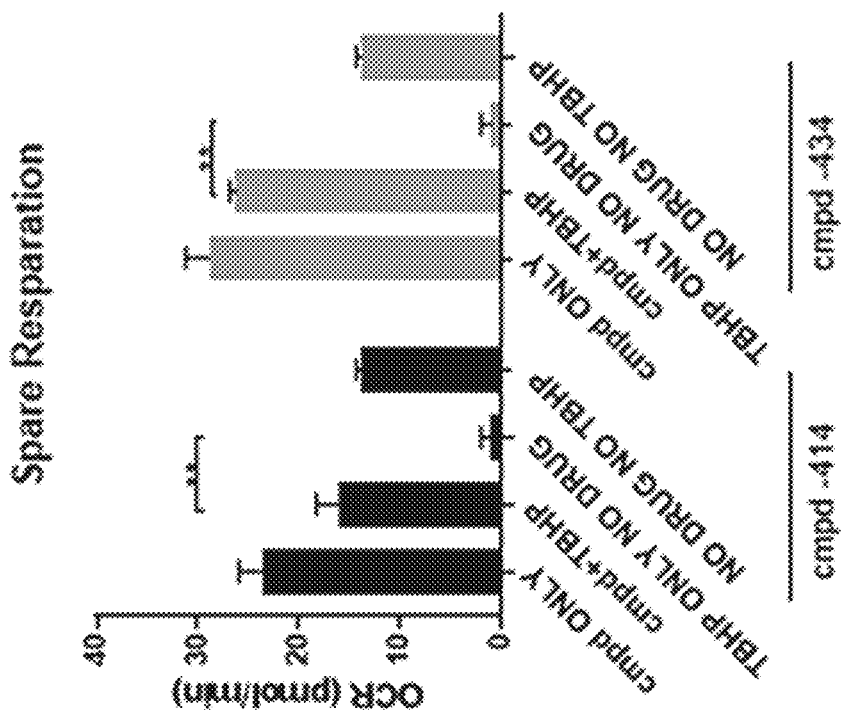
FIGS. 9A-9D demonstrate that compound 414 and 434 improve mitochondrial function after oxidative stress-induced cell death in human retinal pigment epithelial (RPE) cells. Human ARPE-19 cells were preincubated with 0.6 μM of compound 414 and 434 for 18 hours, then treated with 300 μM tert-butyl hydroperoxide (TBHP) for 24 hours. Oxygen consumption rate was determined using the Seahorse XF analyzer to measure mitochondrial function.
Figure 9B:
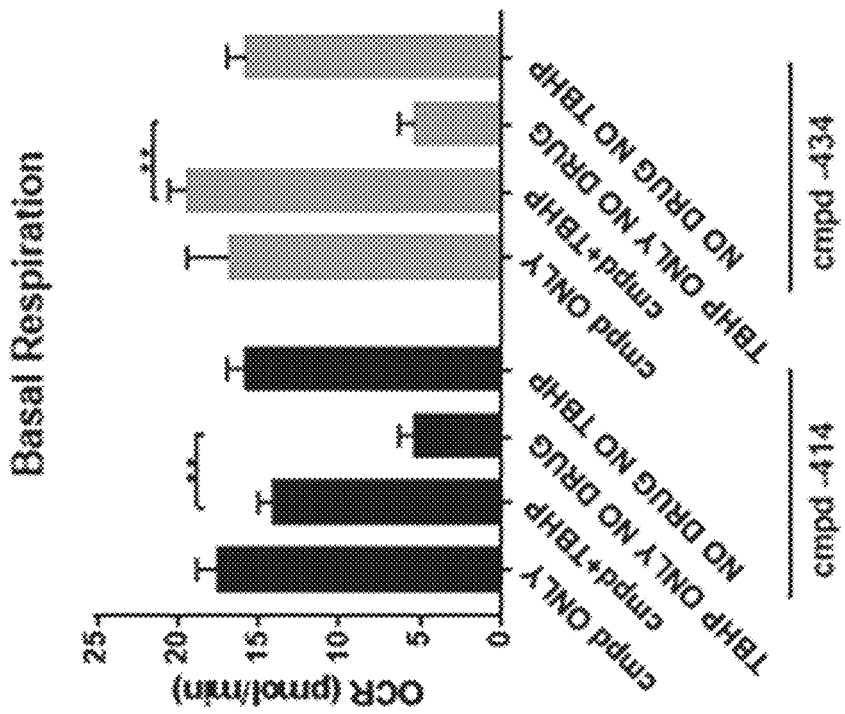
Figure 9D:
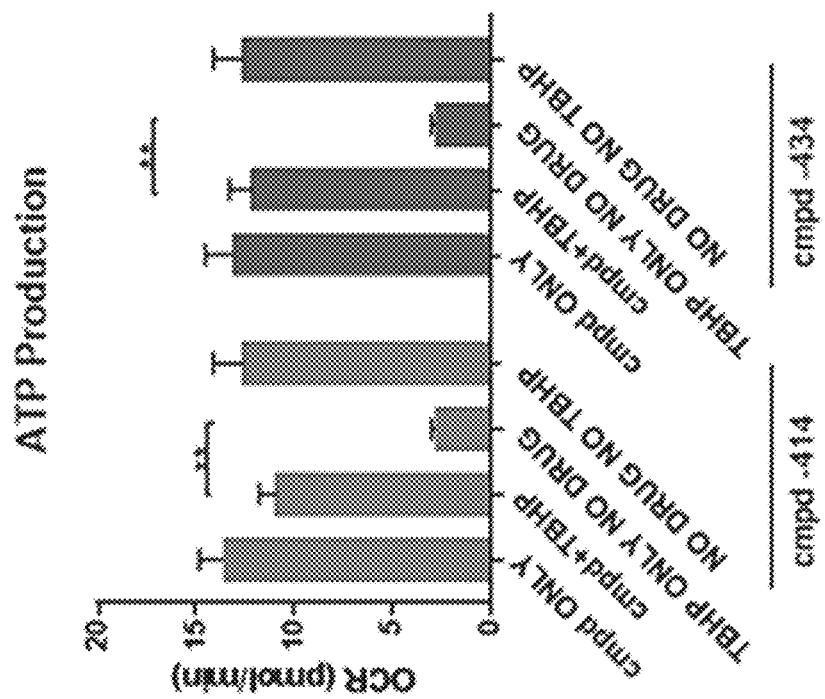
Figure 9C:
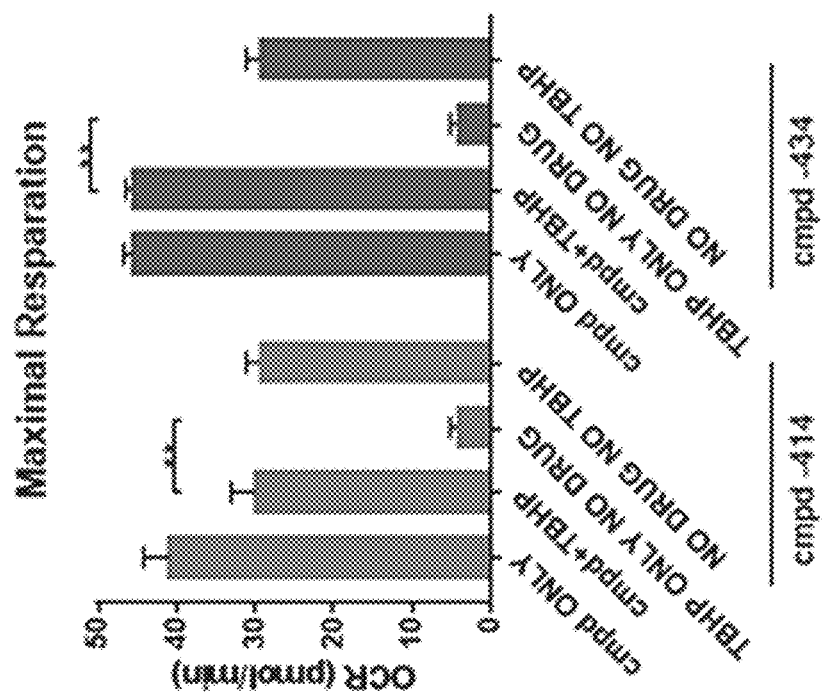

Example 5: Ciclopirox Olamine Improves Mitochondrial Function in Human IPSC-Derived RPE Cells after Oxidative Stress-Induced Cells Death After exposure to TBHP for 24 hours, treatment with ciclopirox olamine protects human iPSC-derived RPE cells from oxidative stress-induced cell death (FIG. 7A). Treatment with ciclopirox olamine significantly increased basal respiration, maximal OCR, reserve capacity, and ATP production after challenge with TBHP in iPSC-derived RPE (FIG. 7A-D).

Example 6: High-Throughput Screen of Chemical Diversity Library

Initial screening of a library with 65,000 synthetic compounds (Chemical Diversity library) using tert-butyl hydroperoxide (TBHP), a chemical oxidizing agent, as a model of oxidative stress-induced cell death. Six imidazopyrimidine and imidazopyrazine derivatives were identified as compounds that significantly protects ARPE-19 cells from TBHP-induced cell death and the protective effects of two (2) of these compounds, C325-0414 (compound 414) and C325-0434 (compound 434) were further investigated.

Example 7: Compounds 414 and 434 Protect Human Retinal Pigment Epithelial (RPE) Cells from Oxidative Stress-Induced Cell Death After exposure to TBHP for 24 hours, treatment with compound 414 protects ARPE-19 cells from oxidative stress-induced cell death (FIG. 8A). Treatment with compound 414 also helps to preserve a normal morphology after challenge with TBHP (FIG. 8E).

Example 8: Compounds 414 and 434 Improve Mitochondrial Function after Oxidative Stress-Induced Cell Death in Human RPE Cells The effects of compound treatment on mitochondrial function in human RPE cells were investigated. Human ARPE-19 cells were preincubated with 0.6 µM of compound 414 or compound 434 for 18 hours, then treated with 300 µM TBHP for 24 hours and oxygen consumption rate determined using the Seahorse XF analyzer. Treatment with compound 414 or compound 434 significantly increased basal respiration, maximal OCR, reserve capacity, and ATP production after challenge with TBHP (FIG. 9A-D).

Example 9: Compounds 414 and 434 Protect Human RPE Cells from UV-B Light Damage

Figure 10:
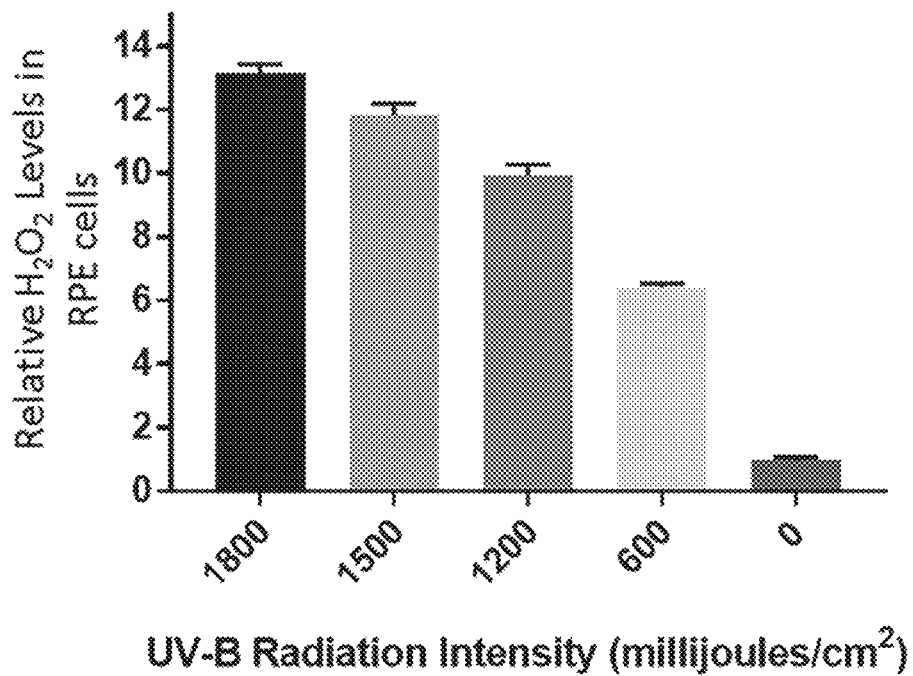
FIG. 10 shows that UV-B radiation causes increases in reactive oxygen species (ROS) production in RPE cells. Human ARPE-19 cells were cultured in complete DMEM for 24 hours and then exposed to various doses of UV-B radiation. These data show that UV-B light can be used to create oxidative stress in RPE cells.
Figure 11:
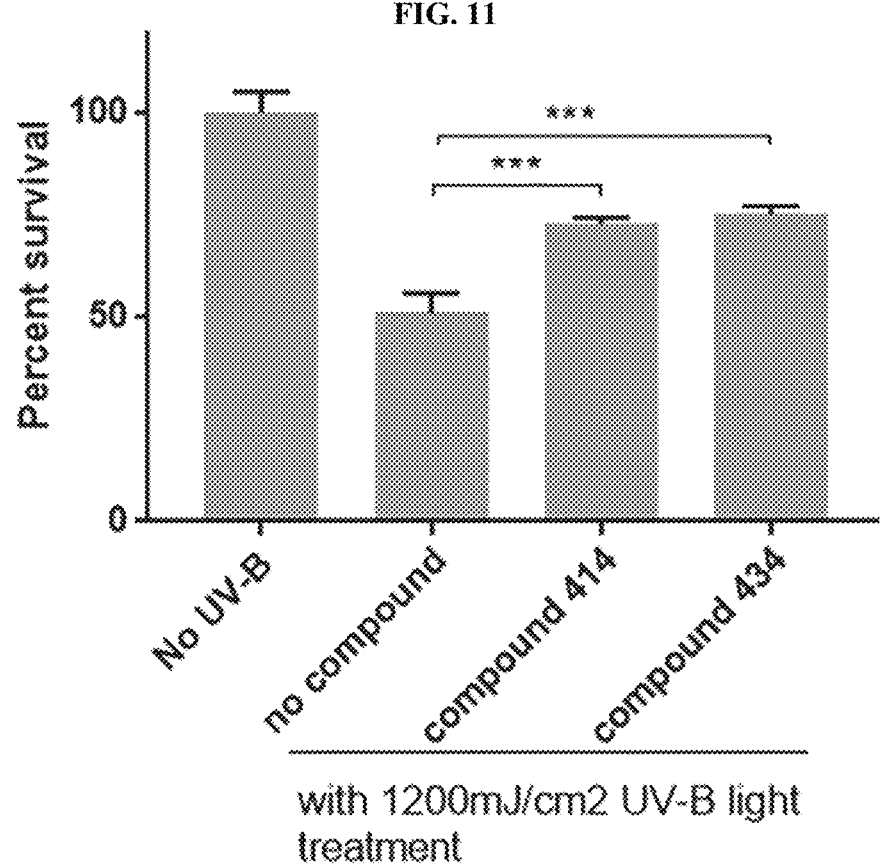
FIG. 11 shows that compound 414 and 434 protect human retinal pigment epithelial (RPE) cells from UV-B radiation damage. Human ARPE-19 cells were preincubated with 0.6 μM of compound 414 or 434 for 24 hours and then exposed to UV-B radiation (1200 mJ/cm$^2$). Protective effect of compound 414 and 434 on human RPE cells exposed to UV-B radiation (1200 mJ/cm$^2$). ****P<0.0001
Figure 12B:
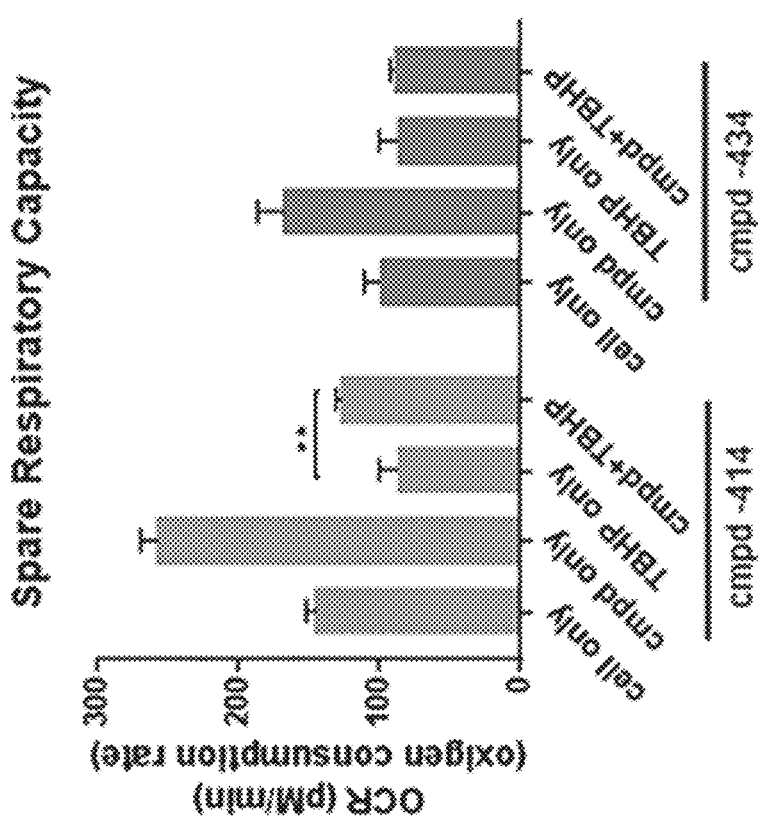
FIGS. 12A-12D show that compound 414 and 434 improve mitochondrial function in human induced pluripotent stem cell-derived RPE (iPSC-derived RPE) cells after oxidative stress-induced cells death. Human iPSC-derived RPE cells were preincubated with 0.6 μM compound 414 or 434 for 18 hours, then treated with 300 μM tert-butyl hydroperoxide (TBHP) for 24 hours. Oxygen consumption rate was determined using the Seahorse XF analyzer to measure mitochondrial function.
Figure 12A:
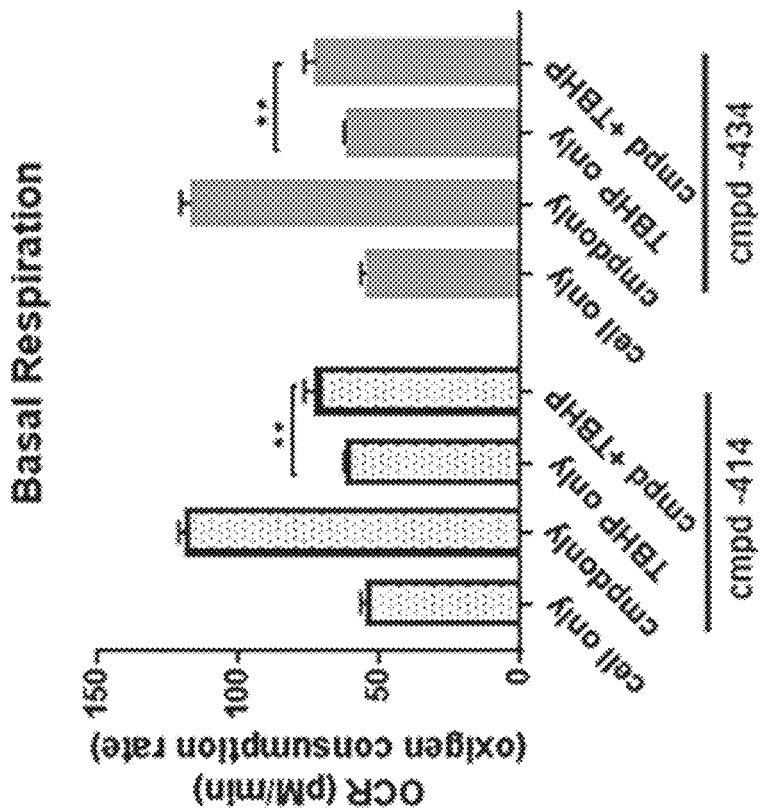
Figure 12C:
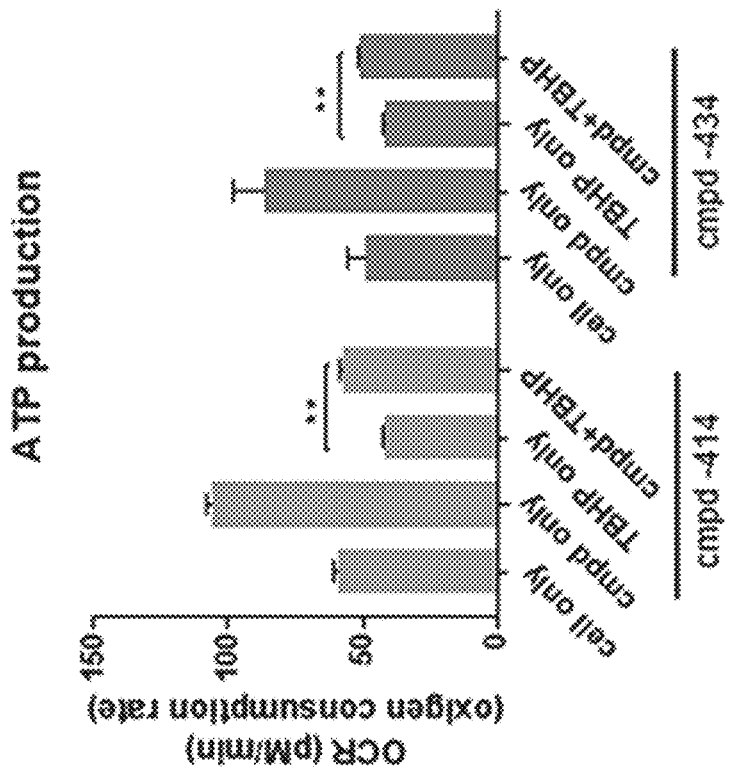
Figure 12D:
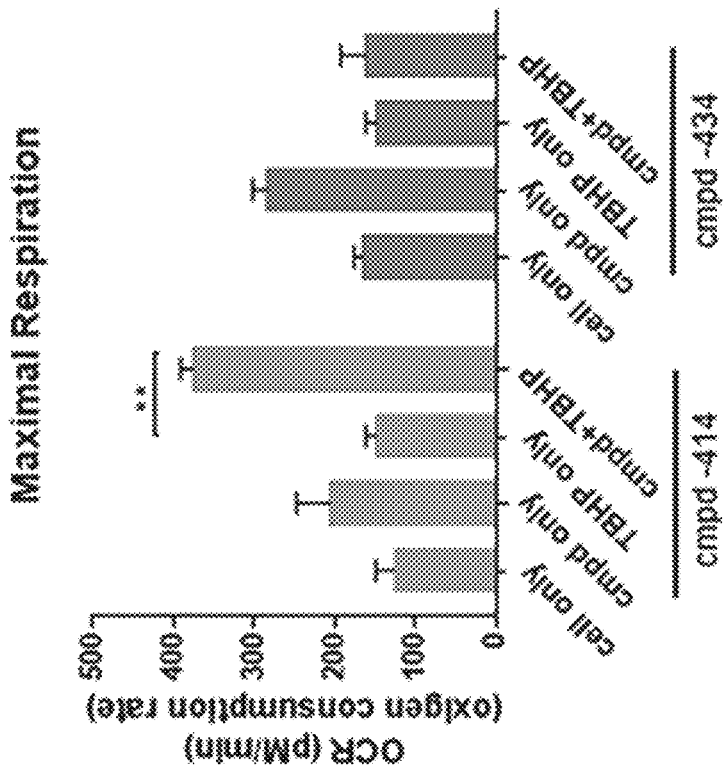

To confirm the results using TBHP, another model of oxidative stress in which human RPE cells are exposed to UV-B light was employed. FIG. 10 shows the generation of ROS at varying doses of UV-B radiation exposure in RPE cells. Human ARPE-19 cells were then preincubated with 0.6 µM of compound 414 and compound 434 for 24 hours and then exposed to 1200 mJ/cm$^2$ of UV-B radiation. Compound 414 and compound 434 protective human ARPE-19 cells exposed to 1200 mJ/cm$^2$ UV-B radiation (FIG. 11).

Example 10: Compounds 414 and 434 Improve Mitochondrial Function in Patient-Specific IPSC-Derived RPE Cells Human iPSC-derived RPE cells were preincubated with 0.6 µM of compound 414 or compound 434 for 18 hours, then treated with 300 µM TBHP for 24 hours and oxygen consumption rate determined using the Seahorse XF analyzer. Treatment with compound 414 significantly increased basal respiration, maximal OCR, reserve capacity, and ATP production after challenge with TBHP (FIG. 12A-12D). Treatment with compound 434 significantly increased basal respiration and ATP production.

Figure 13:
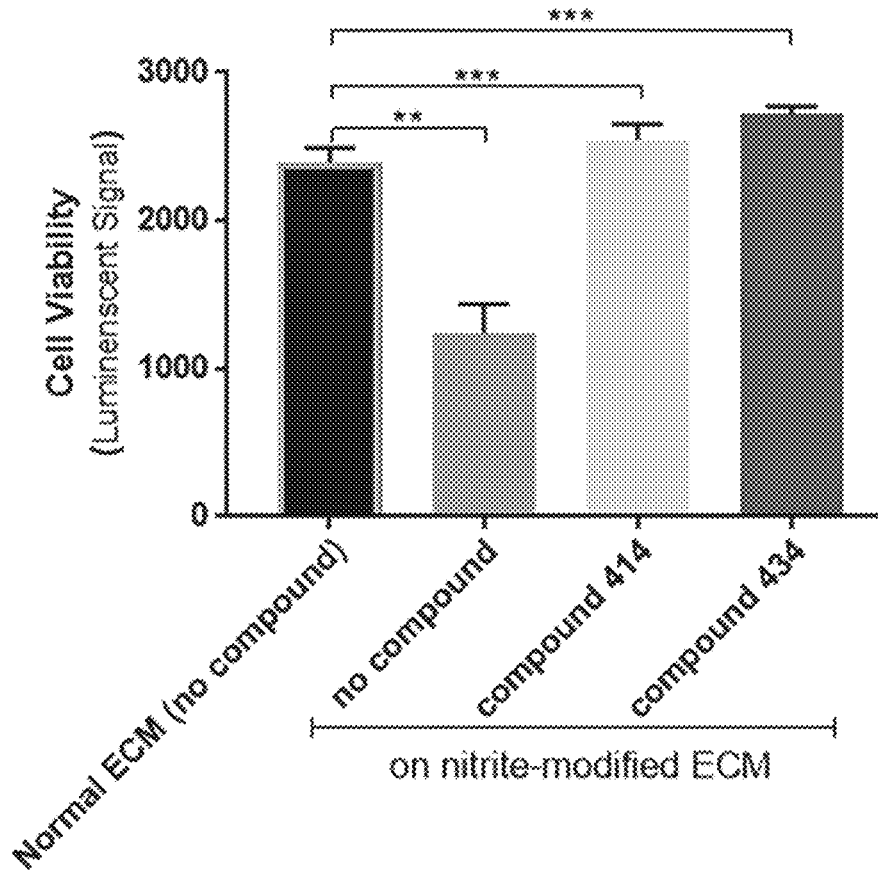
FIG. 13 is a graph illustrating how treatment with compound 414 and 434 enhance human retinal pigment epithelial (RPE) cell viability on nitrite-modified extracellular matrix (ECM). Human ARPE-19 cells were treated with 0.9 μM of compound 414 and 434 and then seeded onto nitrite-modified ECM and untreated (normal) ECM for 24 hours. Protective effects of compound 414 and 434 on ARPE-19 cells seeded onto nitrite-modified ECM. p<0.001; *p<0.0001

Example 11: Compounds 414 and 434 Enhance Human RPE Cell Viability on Nitrite-Modified ECM Reactive nitrogen species (RNS) act together with reactive oxygen species (ROS) to damage cells, causing nitrosative stress. Bruch's membrane aging, which is caused by many factors including nitrosative/oxidative stress, results in damage to RPE cells and affects cell survival. Model systems that mimic the effects of Bruch's membrane aging, a hallmark of AMD, have been used to determine these deleterious effects on cell function and pathology of the overlying retinal pigment epithelium. Non-enzymatic nitration of basement membrane proteins induces RPE cell dysfunction in vitro, thus making this RPE-derived ECM model pertinent to the age-related changes seen in the Bruch's membrane and overlying RPE cells in AMD. FIG. 13 demonstrates the effects of compounds 414 and 434 in this model. Human ARPE-19 cells were seeded onto nitrite-modified ECM and untreated (normal) ECM and treated with 0.9 µM of the compounds for 24 hours. Compounds 414 and 434 enhances cell viability on nitrite-modified ECM (FIG. 13).

Example 12: Cytotoxicity Levels in Human RPE Cells Treated with Tert-Butyl Hydroperoxide and Compounds 414 and 434

Figure 14:
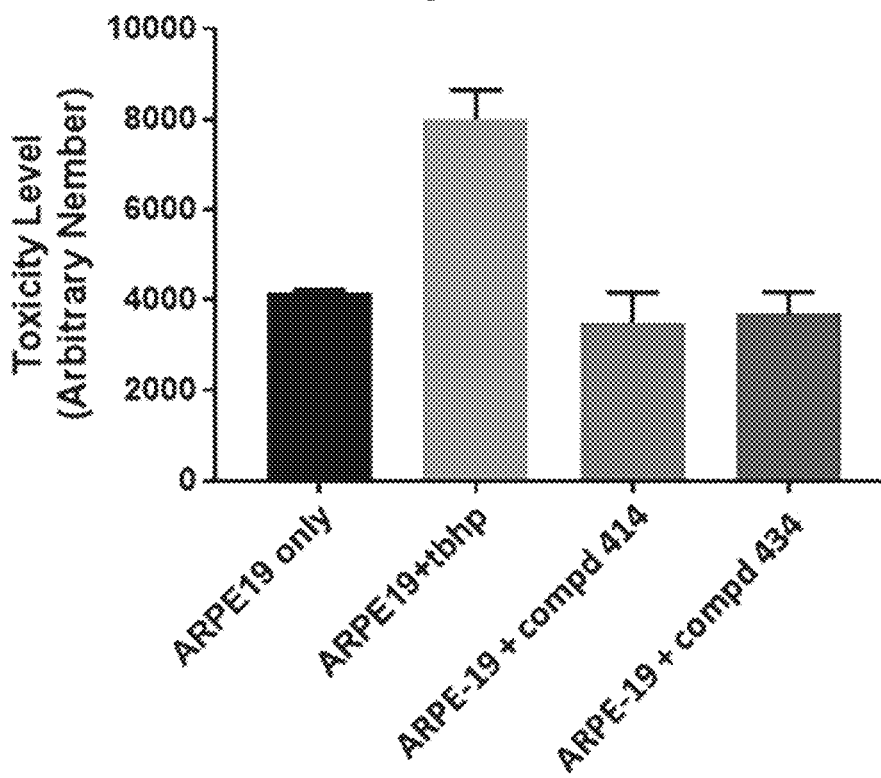
FIG. 14 is a graph illustrating cytotoxicity level of the compounds in human retinal pigment epithelial (RPE) cells. Human ARPE-19 cells were preincubated with 0.9 μM of compound 414 or 434 for 24 hours and then exposed to 300 μM tert-butyl hydroperoxide (TBHP) for 24 hours. Cell toxicity was measured in human ARPE-19 cells after treatment with TBHP and compounds 414 and 434.

After exposure to TBHP for 24 hours and treatment with compound 414 or 434 cytotoxicity levels were measured in human ARPE-19 cells (FIG. 14). Treatment with compound 414 and 434 alone reduce cytotoxicity in human ARPE-19 cells (FIG. 14).

Example 13: Dose-Response Curve of Compound 434

Figure 15:
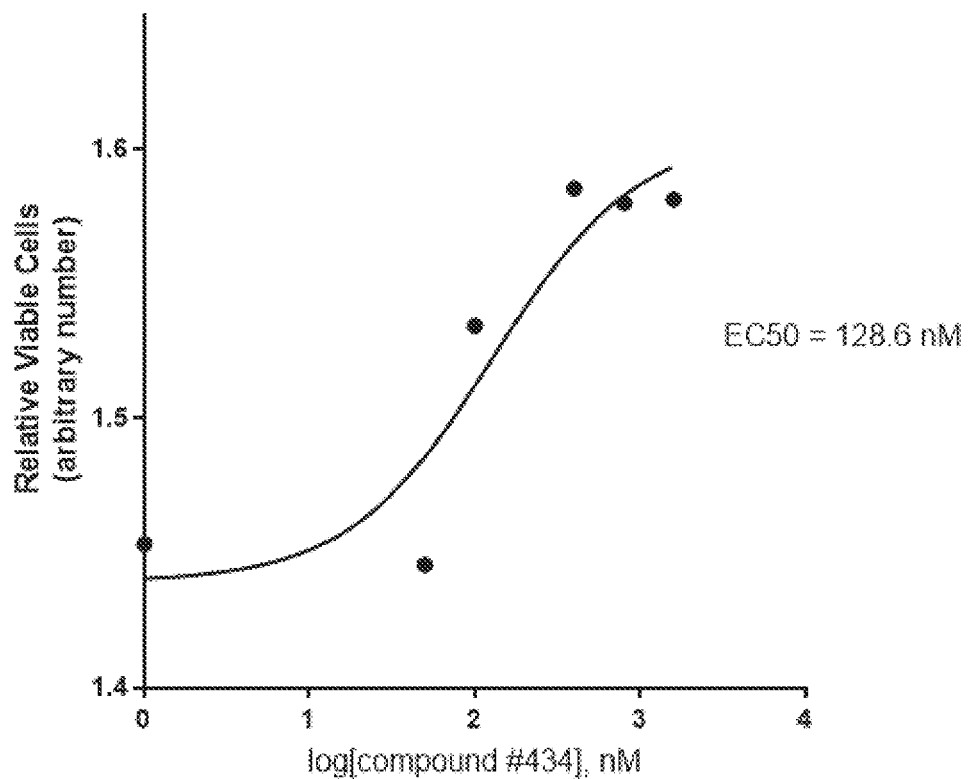
FIG. 15 is a dose-response curve of compound 434.

Human ARPE-19 cells were cultured in complete DMEM for 24 hours and then exposed to 1200 millijoules/cm$^2$ UV-B radiation. 0-1.6 µM of compound 434 was used for dose-response curve (FIG. 15).

Example 14: Dose-Response Curve of Compound 414

Figure 16:
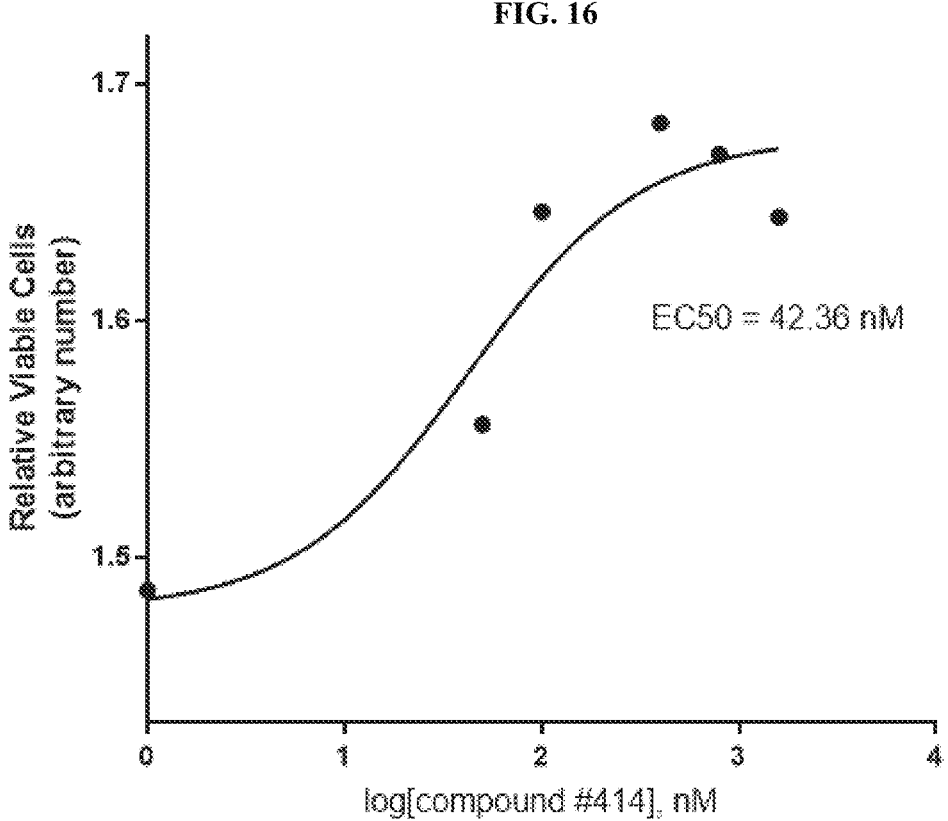
FIG. 16 is a dose-response curve of compound 414.
Figure 17:
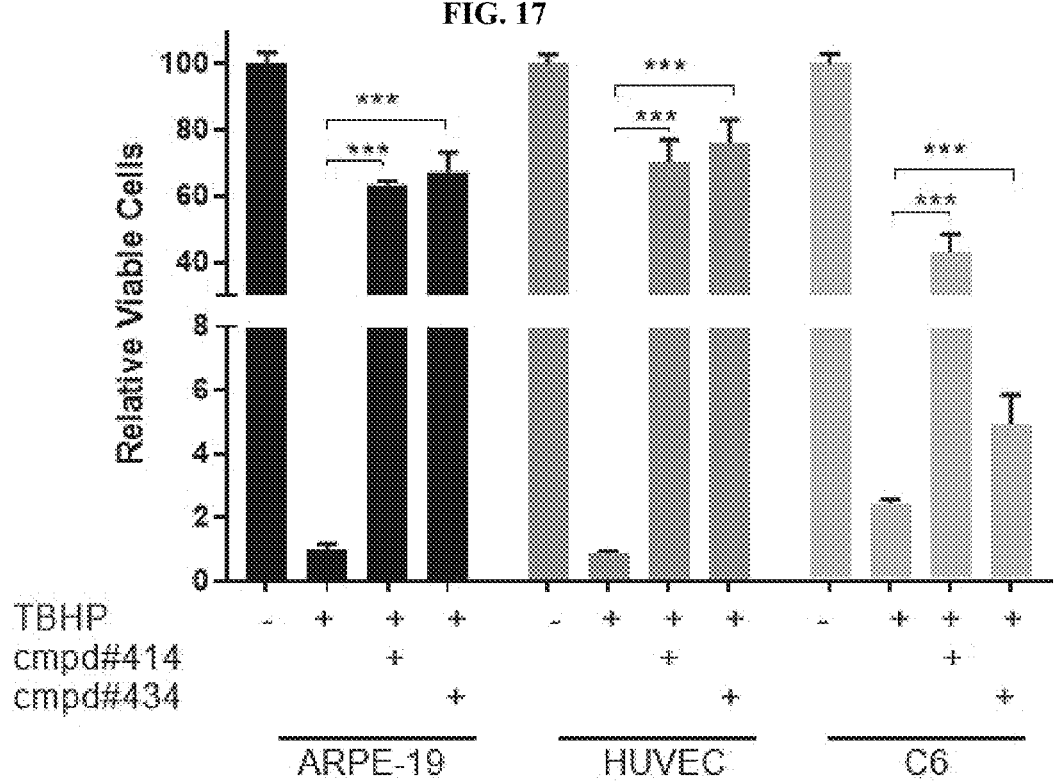
FIG. 17 is a graph illustrating that Compound 414 and 434 protect various cell types from oxidative stress-induced cell death. Human ARPE-19, HUVEC, and C6 cells were preincubated with compound 414 and 434 for 24 hours, and then exposed to 400 μM tert-butyl hydroperoxide (TBHP) to induce cell death for 24 hours. Protective effects of compound 414 and 434 on ARPE-19, HUVEC, and C6 cells exposed to 0.9 μM. ***p<0.01.

Human ARPE-19 cells were cultured in complete DMEM for 24 hours and then exposed to 1200 millijoules/cm$^2$ UV-B radiation. 0-1.6 µM of compound 414 was used for dose-response curve (FIG. 16).

Example 15: Compounds 414 and 434 Protect Various Cell Types from Oxidative Stress-Induced Cell Death Human ARPE-19, HUVEC, and C6 cells were preincubated with compound 414 and 434 for 24 hours, and then exposed to 400 µM tert-butyl hydroperoxide (TBHP) to induce cell death for 24 hours. Protective effects of compound 414 and 434 on ARPE-19, HUVEC, and C6 cells exposed to 0.9 µM. ***p<0.01

Example 16: Ciclopirox Olamine Protects Corneal Endothelial Cells from Oxidative Stress-Induced Cell Death Lens Epithelial Cell Culture Immortalized human lens epithelial cells (CRL-11421) obtained from the American Type Culture Collection (ATCC, Manassas, Va., USA) were cultured in Eagle's minimum essential media (EMEM, ATCC) containing 10% fetal bovine serum (FBS), 100 IU/mL penicillin, 100 µg/mL streptomycin, 100 µg/mL gentamicin, and 2.5 µg/mL amphotericin B (Thermo Fisher Scientific).

Corneal Endothelial Cell Culture

Immortalized cow corneal endothelial cells (CRL-2048) obtained from the American Type Culture Collection (ATCC, Manassas, Va., USA) were cultured in Dulbecco's modified Eagle's medium (DMEM; Thermo Fisher Scientific, Waltham, Mass.) containing 10% fetal bovine serum (FBS), 100 IU/mL penicillin, 100 µg/mL streptomycin, 100 µg/mL gentamicin, and 2.5 µg/mL amphotericin B (Thermo Fisher Scientific).

Induction of Oxidative Stress Using Tert-Butyl Hydroperoxide

Human ARPE-19 cells were plated in 96-well plates for 24 hours in DMEM supplemented with FBS and antibiotics. ARPE-19 cells were preincubated with either ciclopirox olamine (Sigma), compound 414 (Chemical Diversity, San Diego, Calif.), compound 434 (Chemical Diversity) or no compound for 24 hours and then exposed to varying concentrations of tert-butyl hydroperoxide (TBHP; Sigma-Aldrich, St. Louis, Mo.) the next day for 24 hours. Cell viability was measured the following day by REALTIME-GLO™ MT cell viability assay (Promega, Madison, Wis.) using a BioTek FLX800™ fluorescence reader (BioTek Winooski, Vt.).

Statistical Analysis

All experiments were conducted at least three times with triplicates. Independent, two-tailed t tests were performed using Prism (GraphPad Software, Inc., La Jolla, Calif.). A criterion of α=0.05 was adopted.

Selected Results

Figure 18:
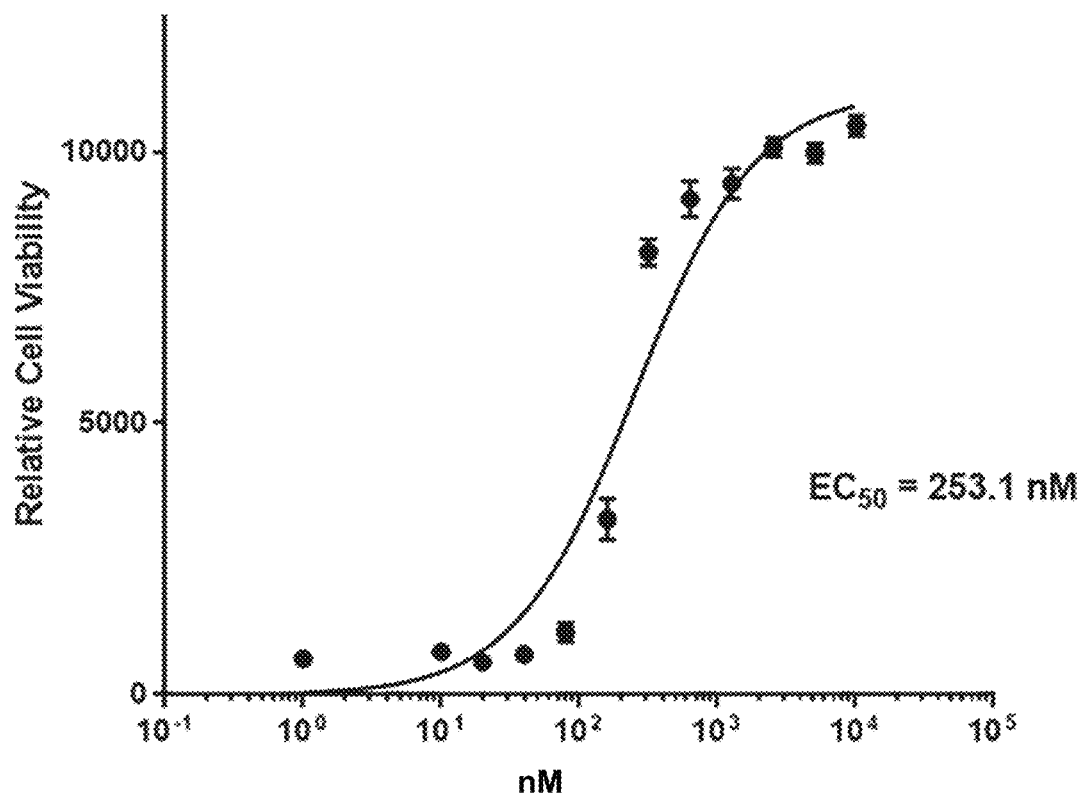
FIG. 18 is a graph illustrating the finding that ciclopirox olamine protects corneal endothelial cells from oxidative stress-induced cell death. Human corneal endothelial cells were preincubated with 0.9 μM ciclopirox olamine for 24 hours and then exposed to 300 M tert-butyl hydroperoxide (TBHP) to induce cell death for 24 hours. Protective effect of 0.9 μM ciclopirox olamine on lens epithelial cells exposed to 300 μM TBHP. Ciclopirox olamine significantly increases cell viability in lens epithelial cells exposed to TBHP.

As demonstrated in FIG. 18, human corneal endothelial cells were preincubated with 0.9 µM ciclopirox olamine for 24 hours and then exposed to 300 M tert-butyl hydroperoxide (TBHP) to induce cell death for 24 hours. Protective effect of 0.9 µM ciclopirox olamine on lens epithelial cells exposed to 300 µM TBHP. Ciclopirox olamine significantly increases cell viability in lens epithelial cells exposed to TBHP, thus protecting corneal endothelial cells from oxidative stress-induced cell death.

Figure 19:
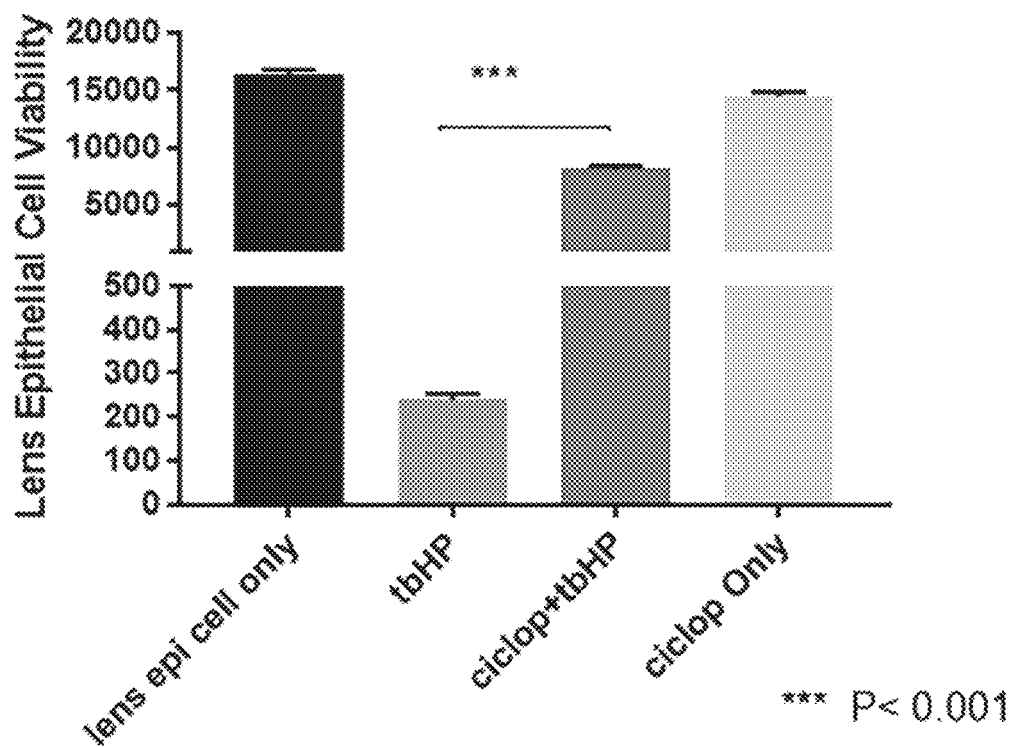
FIG. 19 is a graph illustrating the finding that ciclopirox olamine protects lens epithelial cells from oxidative stress-induced cell death. Human lens epithelial cells were preincubated with 0.9 μM ciclopirox olamine for 24 hours and then exposed to 300 M tert-butyl hydroperoxide (TBHP) to induce cell death for 24 hours. Protective effect of 0.9 μM ciclopirox olamine on lens epithelial cells exposed to 300 μM TBHP. Ciclopirox olamine significantly increases cell viability in lens epithelial cells exposed to TBHP. ***p<0.001.

As demonstrated in FIG. 19, human lens epithelial cells were preincubated with 0.9 µM ciclopirox olamine for 24 hours and then exposed to 300 M tert-butyl hydroperoxide (TBHP) to induce cell death for 24 hours. Protective effect of 0.9 µM ciclopirox olamine on lens epithelial cells exposed to 300 µM TBHP. Ciclopirox olamine significantly increases cell viability in lens epithelial cells exposed to TBHP, thus protecting corneal endothelial cells from oxidative stress-induced cell death.

Figure 20A:
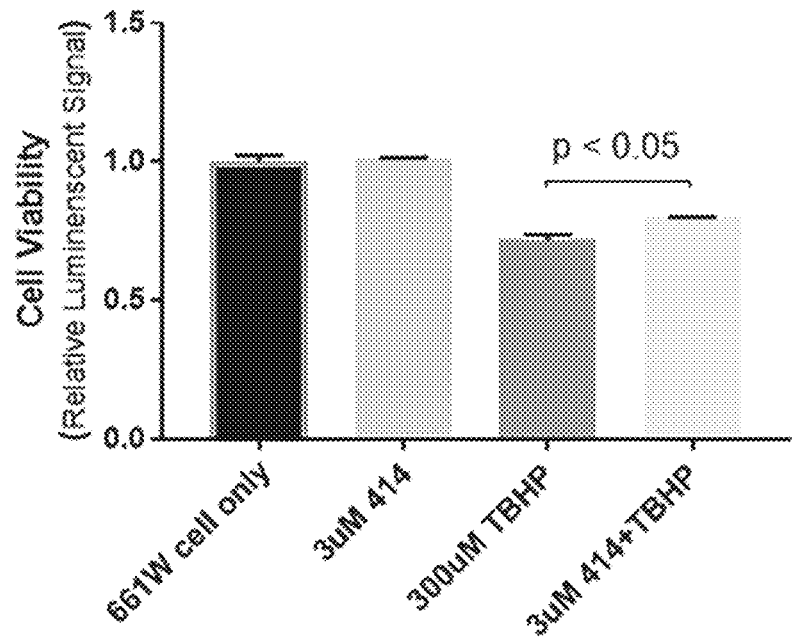
FIGS. 20A-20B illustrate that certain compounds of the invention (compound 414, FIG. 20A, and compound 434, FIG. 20B) protect photoreceptor cells from oxidative stress-induced cell death.
Figure 20B:
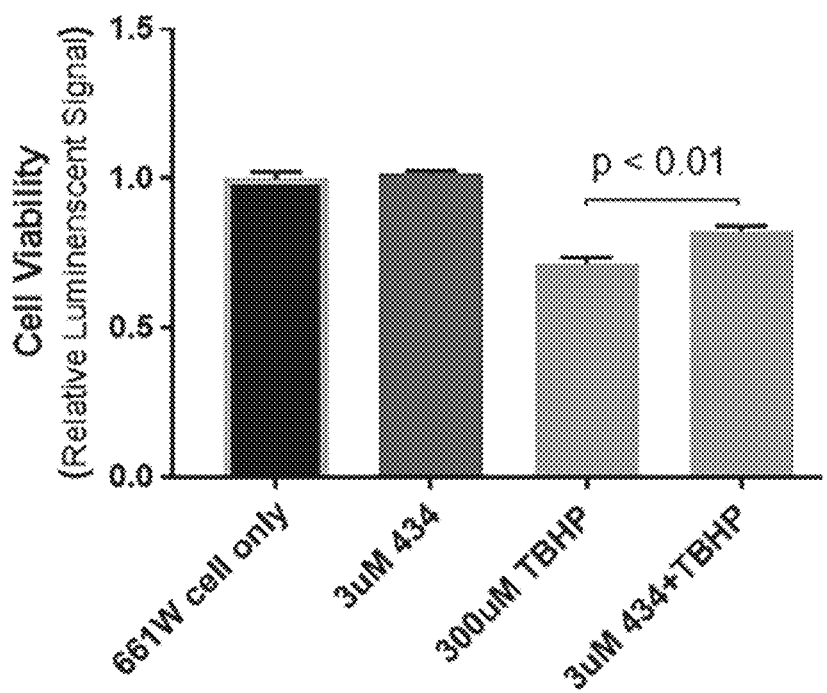

Example 17: Compound 414 and 434 Protect Photoreceptor Cells from Oxidative Stress-Induced Cell Death: Implications for Retinal Degenerations As shown in FIGS. 20A-20B, compounds 414 and 434 protect 661W photoreceptor-derived cells from tert-butyl hydroxide-induced oxidative stress. Retinal photoreceptor-derived cell line (661W) were cultured until confluent in Dulbecco's modified eagle medium (DMEM) with 10% fetal bovine serum (FBS). Murine photoreceptor-derived cells were preincubated with 3 µM ciclopirox olamine for 24 hours and then exposed to 300 µM tert-butyl hydroperoxide (TBHP) to induce cell death for 24 hours. Compound 414 (FIG. 20A) and compound 434 (FIG. 20B) significantly increased cell viability of photoreceptor-derived cells after exposure to TBHP. Bar: standard error, n=4. student t-test was performed for statistical analysis.

Example 18: Preparation of Ciclopirox Solution in Hydroxypropyl Beta Cyclodextrin Preparation of Hydroxypropyl Beta Cyclodextrin (HPBCD), 40%

2.00 g HPBCD was dissolved in 4 mL deionized filtered water by slow inversion/rotation. After 1 h of slow inversion, the solid had dissolved to provide a clear solution. The volume was adjusted to 5.00 mL to provide 5.00 mL of a 40% clear solution by weight.

Preparation of Stock Ciclopirox 35 Mg/Ml in 40% Hydroxypropyl Beta Cyclodextrin

To the 5.00 mL solution of 40% HPBCD was added 175 mg (0.844 mmol, MW 207.3) ciclopirox powder and the vial sealed and placed under slow rotary inversion to dissolve the solid. After 1 hour mixing the ciclopirox had completely dissolved to give a solution of 35 mg/mL ciclopirox in 40% HPBCD. It is worth noting that the solubility of ciclopirox in pH 7.4 phosphate buffer (no saline) is only 1.0 mg/mL. This 35 mg/mL solution was easily filtered through a 0.22 um syringe filter (MILLEX GV, PVDF membrane).

The filtered solution was then checked for pH and a high value of approx. 8.3 was noted, and the pH adjusted under stirring to 7.4 by the addition of a total of 0.5 mL 1M HCl. The pH 7.4 adjusted solution of 35 mg/mL ciclopirox in 40% HPBCD (osmolarity 0.670) was diluted incrementally with deionized water until the osmolarity was 0.376 with a resulting concentration of 21.3 mg/mL. The total volume of 175 mg ciclopirox was thus prepared at 21.3 mg/mL in 8.2 mL volume. Since the addition of water was necessary to reduce the osmolarity, the concentration of HPBCD was now 24%. A final solution of 21.3 mg/mL ciclopirox in 24%

HPBCD, total volume of 8.2 mL, was partitioned into 1 mL sample vials. The solution may be frozen at −80° C. and thawed at room temperature.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or ameliorating retinal degeneration in a subject,
   the method comprising administering topically to the eye of the subject an ophthalmologically acceptable pharmaceutical composition comprising ciclopirox (6-cyclohexyl-1-hydroxy-4-methyl-2(1H)-pyridone), or a salt or solvate thereof, and at least one compound selected from the group consisting of hydroxypropyl-alpha-cyclodextrin and hydroxypropyl-beta-cyclodextrin.

2. The method of claim 1, wherein the retinal degeneration comprises age-related macular degeneration (AMD).

3. A method of treating or ameliorating an anterior segment ocular disorder in a subject,
   the method comprising administering topically to the eye of the subject an ophthalmologically acceptable pharmaceutical composition comprising ciclopirox (6-cyclohexyl-1-hydroxy-4-methyl-2(1H)-pyridone), or a salt or solvate thereof, and at least one compound selected from the group consisting of hydroxypropyl-alpha-cyclodextrin and hydroxypropyl-beta-cyclodextrin.

4. The method of claim 3, wherein the disorder comprises at least one selected from the group consisting of Fuchs Endothelial Corneal Dystrophy, cataracts, glaucoma, and keratoconus.

5. The method of claim 1, wherein at least one applies:
   the composition has pH of about 5-8;
   the composition further comprises a thickening agent.

6. The method of claim 3, wherein at least one applies:
   the composition has pH of about 5-8;
   the composition further comprises a thickening agent.

7. The method of claim 1, wherein the ophthalmologically acceptable formulation further comprises at least one analgesic agent.

8. The method of claim 1, wherein the ophthalmologically acceptable formulation further comprises at least one antibacterial or antifungal agent.

9. The method of claim 1, wherein the ciclopirox is ciclopirox olamine.

* * * * *